(12) United States Patent
Lindner et al.

(10) Patent No.: US 10,765,709 B2
(45) Date of Patent: Sep. 8, 2020

(54) COMPOSITIONS AND METHODS FOR THE TREATMENT OR PREVENTION OF OXALATE-RELATED DISORDERS

(71) Applicant: OXTHERA INTELLECTUAL PROPERTY AB, Stockholm (SE)

(72) Inventors: Elisabeth Lindner, Stockholm (SE); Maria Åkerman, Sollentuna (SE); Anna Sjögren, Stockholm (SE); Orla McCallion, Vallentuna (SE)

(73) Assignee: OXTHERA INTELLECTUAL PROPERTY, Stockholm (DE)

( * ) Notice: Subject to any disclaimer, the term of this patent is extended or adjusted under 35 U.S.C. 154(b) by 0 days.

(21) Appl. No.: 16/308,439

(22) PCT Filed: Jun. 13, 2017

(86) PCT No.: PCT/EP2017/064422
§ 371 (c)(1),
(2) Date: Dec. 7, 2018

(87) PCT Pub. No.: WO2017/216165
PCT Pub. Date: Dec. 21, 2017

(65) Prior Publication Data
US 2019/0125807 A1    May 2, 2019

(30) Foreign Application Priority Data
Jun. 13, 2016 (SE) ...................... 1650828

(51) Int. Cl.
*A61K 35/74* (2015.01)
*A61P 1/00* (2006.01)
*A61K 9/48* (2006.01)

(52) U.S. Cl.
CPC ............ *A61K 35/74* (2013.01); *A61K 9/4866* (2013.01); *A61K 9/4891* (2013.01); *A61P 1/00* (2018.01)

(58) Field of Classification Search
None
See application file for complete search history.

(56) References Cited

U.S. PATENT DOCUMENTS

| 6,200,562 | B1 | 3/2001 | Allison et al. | |
| 6,242,230 | B1* | 6/2001 | Batich | ............... A61K 9/1652 |
| | | | | 264/4.32 |
| 6,355,242 | B1 | 3/2002 | Allison et al. | |
| 8,545,836 | B2* | 10/2013 | Kaul | ................. A61K 9/1623 |
| | | | | 424/93.1 |

FOREIGN PATENT DOCUMENTS

| EP | 1 771 201 B1 | 8/2014 |
| WO | WO-2005/097176 A2 | 10/2005 |
| WO | WO-2007/070052 A2 | 6/2007 |
| WO | WO-2007/070677 A2 | 6/2007 |
| WO | WO-2014/113648 A1 | 7/2014 |

OTHER PUBLICATIONS

Hatch et al. "Enteric oxalate elimination is induced and oxalate is normalized in a mouse model of primary hyperoxaluria following intestinal colonization with Oxalobacter," Am. J. Physiol. Gastrointest. Liver Physiol., vol. 300, pp. G461-G469 (2011) (First published Dec. 2010).

Hatch et al., "A human strain of Oxalobacter (HC-1) promotes enteric oxalate secretion in the small intestine of mice and reduces urinary oxalate excretion," Urolithiasis, vol. 41, pp. 379-384 (2013) (Published online Aug. 2013).

Sidhu et al. "Rapid Reversal of Hyperoxaluria in a Rat Model After Probiotic Administration of Oxalobacter Formigenes," The Journal of Urology, vol. 166, pp. 1487-1491 (Oct. 2001).

Vaidyanathan et al. "Hyperoxaluria, Hypocitraturia, Hypomagnesuria, and Lack of Intestinal Colonization by Oxalobacter Formigenes in a Cervical Spinal Cord Injury Patient with Suprapubic Cystomy, Short Bowel, and Nephrolithiasis," The Scientific World Journal, vol. 6, pp. 2403-2410 (2006).

* cited by examiner

Primary Examiner — Heidi Reese
(74) Attorney, Agent, or Firm — Foley & Lardner LLP

(57) ABSTRACT

The present disclosure is related to pharmaceutical compositions and methods for treating and/or preventing oxalate-related disorders. More particularly, the present disclosure pertains to compositions comprising an oxalate-degrading bacteria *Oxalobacter formigenes* particularly suitable for the treatment and/or prevention of late stage hyperoxaluria characterized by high plasma-oxalate levels and a progressing decrease in kidney function.

20 Claims, 3 Drawing Sheets

COMPOSITIONS AND METHODS FOR THE TREATMENT OR PREVENTION OF OXALATE-RELATED DISORDERS

CROSS-REFERENCE TO RELATED APPLICATIONS

The present application is the U.S. National Stage of International Application PCT/EP2017/064422, filed Jun. 13, 2017, and claims priority to Sweden Patent Application No. 1650828-5, filed Jun. 13, 2016.

TECHNICAL FIELD

The present disclosure relates to the field of oxalate-related disorders and to pharmaceutical compositions and methods for the treatment or prevention of oxalate-related disorders. More specifically, the present disclosure pertains to the treatment or prevention of calcium-oxalate-deposition related disorder(s), such as calcium-oxalate-deposition related disorder(s) involving hyperoxalemia, and such as chronic kidney disease (CKD). It is also related to the prevention or treatment of oxalate-related inflammation.

BACKGROUND OF THE DISCLOSURE

Oxalate is a metabolic end product which cannot be broken down by humans. The human body has two main excretory organ pathways for oxalate; the kidney and the intestine. Both pathways are controlled by transporter proteins abundant in the tubular and intestinal epithelium. It is of utmost importance that excretion of oxalate through urine and through the intestinal lumen is sustained.

Primary and Secondary hyperoxaluria are two distinct clinical expressions characterized for example by abnormal excretions of oxalate in the urine. Primary hyperoxaluria is an inherited genetic disorder with defective enzyme activities. In contrast, Secondary hyperoxaluria may be caused by a number of factors including increased dietary ingestion of oxalate or precursors of oxalate, or alterations in intestinal absorption or excretion of oxalate or fat and, alterations in intestinal microbiota or genetic variations of intestinal or tubular oxalate transporter protein expression. Hyperoxaluria is a known complication of Inflammatory Bowel Disease (IBD) and hyperoxaluria with hyperoxalemia is a common consequence of resection of parts of the small intestine and Roux-en-Y gastric bypass surgery. The symptoms of these diseases range from unique kidney stones, recurrent kidney stones and nephrocalcinosis to chronic kidney disease (CKD) and end stage renal disease (ESRD).

Secondary Hyperoxaluria

Oxalate-related CKD due to secondary hyperoxaluria is a health problem throughout the world. It is e.g. characterized by progressively increasing concentrations of oxalate in urine leading to kidney stones.

Secondary hyperoxaluria does normally not lead to ESRD unless hyperoxalemia has occurred. This is mostly common in patients with a resected small bowel such as SBS-patients and bariatric surgery patients.

The liver, the major metabolic organ in the body, is the main site of oxalate production. Oxalate is however not further metabolized and must therefore be excreted. This excretion occurs by two routes; through renal tubular excretion and through intestinal excretion; both excretion routes mediated by active transporter proteins from the SLC26 family. The concentration of oxalate in plasma and hence in tubular fluids is critical, e.g. during renal excretion, where increased oxalate concentrations cause risks for the formation of calcium oxalate crystals in the distal tubules and the connecting duct with subsequent formation of calcium oxalate depositions or calcification of the kidney. The intestinal excretion route is particularly important in preventing pathological conditions that involve elevated plasma oxalate concentrations and calcification of soft tissue.

Secondary hyperoxaluria may be caused by a number of factors including increased dietary ingestion of oxalate or precursors of oxalate, or alterations in intestinal absorption or excretion of oxalate or fat and, alterations in intestinal microbiota or genetic variations of intestinal oxalate transporters. Hyperoxaluria is a known complication of Inflammatory Bowel Disease. The disease spectrum extends from recurrent kidney stones, nephrocalcinosis and urinary tract infections to chronic kidney disease and end stage renal disease (Bhasin, 2015). This typically happens in diseases with impaired intestinal excretion due to inflammation such as Inflammatory Bowel Disease, vulvodynia, small intestine bacterial overgrowth (SIBS), gastroenteritis, gastritis, enteritis, enterocolitis, ulcerative colitis, Crohn's disease, and oxalate-related disorder in patients treated with a gastrointestinal lipase inhibitor.

When calcium oxalate burden exceeds the renal excretory ability, calcium oxalate starts to deposit in all body fluids and soft tissue. This is mostly common in patients with a resected small bowel such as Short Bowel Syndrome (SBS) patients, some IBD patients, intestinal cancer patients and bariatric surgery patients.

Also ESRD-patients on dialysis tend to build up plasma oxalate as a consequence of the kidney failure and may also suffer from oxalosis that could affect graft survival in kidney transplantation.

Primary Hyperoxaluria

Primary hyperoxaluria (PH) is a paediatric, seriously debilitating and life-threatening genetic disease with a high unmet medical need. PH is a rare autosomal recessive inborn error of glyoxylate metabolism, with significant morbidity and mortality, especially in young children. PH occurs as a consequence of an increased hepatic production of oxalate and is characterised by widespread calcium oxalate crystallization, progressing hyperoxalemia followed by reduced kidney function. As a result of renal oxalate excretion, patients with PH have high levels of urinary oxalate ($>0.5$ mmol/24 h/1.73 m$^2$ vs. $<0.5$ mmol/24 h/1.73 m$^2$ in healthy patients) [Hoppe, 2012]. Patients with PH have a wide range of oxalate production, reflected by hyperoxaluria ranging from slightly to highly elevated ($>0.5$-4.5 mmol/day, 1.73 m$^2$). The extent of oxalate over-production is partly connected to specific genotypes, of which more than 140 are known. Progression to ESRD has been shown to correlate with age at diagnosis (time for exposure to high oxalate), the level of urinary oxalate excretion and kidney function at diagnosis [Zhao et al., 2016]. Patients with a high urinary oxalate excretion and low estimated glomerular filtration rate (eGFR) at diagnosis tend to progress more quickly to ESRD. In PH patients, plasma oxalate gradually increases from 1-3 µmoles/L at early stages to 45-50 µmoles/L at early ESRD. It is common that plasma oxalate rises as high as 150-300 µmoles/L during ESRD and dialysis treatment, leading to systemic accumulation of oxalate and systemic oxalosis.

Often, the first clinical symptoms of PH are renal tubular disorders, manifested by flank pain and kidney stones. The symptoms are primarily caused by calcium oxalate crystal-mediated inflammation of the tubular epithelial cells and growing calcium oxalate crystal deposition gradually causing calcification of the kidney. Progressive renal damage is caused by a combination of tubular toxicity from oxalate, nephrocalcinosis and renal obstruction by stones, or stone removal procedures [Cochat and Rumsby, 2013; Tang et al., 2015]. There is currently no approved pharmaceutical therapy for treatment of PH. Eventually the only curative therapy, only for PH type 1, is a combined kidney and liver transplantation at ESRD (Cochat et al., 2012). Overall, the median renal survival is 24-33 years [Lieske et al., 2005, Harambat et al., 2010].

There are three known types of PH (Type 1, 2 and 3) with Type 1 being the most severe and most widespread (70-80% of known cases) [Hoppe et al., 2009]. The three types of PH are caused by a deficiency or a mislocalisation of different enzymes affecting the hepatic production of oxalate: Type 1 is caused by a deficiency of liver-specific peroxisomal alanine-glyoxylate aminotransferase, Type 2 by a lack of glyoxylate reductase-hydroxypyruvate reductase and Type 3 by a lack of the liver-specific mitochondrial enzyme 4-hydroxy-2-oxoglutarate aldolase [Cochat and Rumsby 2013, Belostotsky et al., 2010]. The estimated incidence of PH Type 1 is one case per 120,000 live births per year in Europe and the prevalence is one to three per million population [Cochat et al., 1995; Kopp and Leumann, 1995; van Woerden et al., 2003]. Incidence and prevalence may have been underestimated because of underdiagnosis [Leumann and Hoppe, 2001, Hopp et al., 2015].

Declining kidney function results in progressive hyperoxalemia and plasma calcium oxalate supersaturation. The increasing plasma oxalate concentrations cause calcium oxalate deposits to build up in the body. Deposits may be located in the bone, soft tissue, arterial media, peripheral nerves, skin, eyes and the heart [Beck et al., 2013]. Already at early stages in the disease, hyperoxalemia damages cells in the heart, causes calcification (stiffness) and causes inflammation in the myocardium leading to progressive reduced left ventricular strain leading to heart arrhythmia and heart failure (Lagies et al., 2013, Lagies et al., 2014, Lagies et al., 2015).

The interplay between biological molecules and crystal formation is an emerging field of research (see e.g. Aggarwal et al., 2013). In plasma, oxalate may be present as free oxalate, divalent metal-bound free oxalate, protein and lipid-associated oxalate and as solid divalent metal oxalate crystals. The ratio between total oxalate and free oxalate increases with time and disease progression.

After combined liver-kidney transplantation where the new liver produces normal levels of oxalate, an initial decrease of free oxalate is observed. However, when the plasma oxalate concentration is reduced under the saturation limit, calcium oxalate deposits in proteins and lipids, in vessel walls and soft tissue start to dissolve, which results in a new increase of the plasma oxalate concentration. Urinary and plasma oxalate can be elevated for many months to years following transplantation and may lead again to deterioration of the new kidneys (Leumann and Hoppe, 2001). Thus, the prevention of oxalate build-up before and during dialysis and enhancement of excretion of oxalate through the small bowel and through urine is highly beneficial for PH patients. Also for patients with maintained kidney function it is crucial to delay or stop accumulation of calcium oxalate deposition to prevent kidney deterioration.

Secondary Hyperoxaluria with Hyperoxalemia

Gregory et al, 1975, showed that Jejuno-Ileal Bypass (JIB) surgery in otherwise healthy bariatric patients caused renal failure. The elimination of the major intestinal excretion pathway caused high plasma oxalate concentrations, which in turn lead to renal failure. The procedure was discontinued in 1979. Today the dominant procedure for bariatric surgery is Roux-en-Y, a smaller resection of the jejunum/ileum. Although this procedure is associated with recurrent kidney stones, it does not cause ESRD.

Short Bowel Syndrome, SBS, is defined as a disease status where a patient has resected the small bowel and has less than 200 cm bowel left. Similarly to JIB patients, SBS patients have a 45% risk of kidney failure (ESRD) caused by increased concentrations of plasma oxalate.

Zellweger's disease, or the Zellweger spectrum disorders (ZDS) are characterized by a general loss of peroxisomal functions caused by deficient peroxisomal assembly. The disease is heterogeneous in its presentation and survival. Despite a normal level of the enzyme AGT (Alanine:glyoxylate aminotransferase) which is deficient in primary hyperoxaluria, severe hyperoxaluria has been reported in several ZSD patients (van Woerden et al, 2006).

*Aspergillus niger* infection is a rare fungus infection. A *niger* is an oxalate producing organism and can cause plasma oxalate at levels that can lead to ESRD.

Oxalobacter formigenes

*Oxalobacter formigenes* is a strict anaerobic bacterium that relies exclusively on oxalate as a substrate to obtain energy for its survival and growth. It is currently believed to be the most efficient oxalate-reducing enzymatic system that operates at neutral pH. Not all humans carry populations of *O. formigenes* in their intestinal tract. For example, there is a low or a complete lack of oxalate-degrading bacteria in the fecal samples of persons who have had jejunoileal bypass surgery. Administration of *O. formigenes* to a subject in need thereof has been shown to have an effect on dietary oxalate absorption, but it has also been shown to have effect on the elimination of oxalate from plasma to the intestine, promoting the natural intestinal oxalate excretion pathway. *O. formigenes* has furthermore been shown to promote active elimination of oxalate, possibly through interaction with SLC26 transporter proteins that enhance the oxalate flux from plasma to small bowel (Hatch et al., 2011; Hatch and Freel, 2013).

Compositions comprised of oxalate-degrading bacteria, such as *O. formigenes* for use in methods for reducing urinary and plasma oxalate for treating oxalate-related conditions have previously been disclosed in the art, such as in U.S. Pat. Nos. 6,200,562, 6,355,242, WO2007075447, and WO2005123114.

There is however still a need for improved compositions for treating oxalate-related disorders, particularly for treating or preventing calcium-oxalate deposition related disorders, such as calcium-oxalate deposition related disorder(s) involving hyperoxalemia as well as treating ESRD patients on dialysis. There is also a need for pharmaceutical compositions that may enhance or increase the excretion of oxalate to reduce the systemic oxalate burden and the related inflammation in patients with calcium oxalate deposition.

SUMMARY OF THE DISCLOSURE

The problems in the art in relation to the treatment and prevention of oxalate related disorders, or more particularly calcium-oxalate deposition related disorders such as calcium-oxalate deposition related disorders involving hyperoxalemia, have now been overcome or at least mitigated by the provision herein of pharmaceutical compositions and drug products, particularly in the form of new enteric-coated capsules, comprising said pharmaceutical compositions. Sustained excretion of oxalate is crucial in patients suffering from said disorders.

Surprisingly, the pharmaceutical compositions and drug products disclosed herein are proposed to dissolve calcium oxalate crystals and increase the excretion of oxalate from body fluids, e.g. urinary oxalate, thereby delaying or stopping progressive decline in kidney function, particularly in patients with Chronic Kidney Disease.

There are also provided methods and uses encompassing the pharmaceutical compositions and drug products of the present disclosure. There is furthermore provided a manner to treat or prevent oxalate-related inflammation.

There is provided herein improved means for treating calcium-oxalate deposition related disorders which are commonly associated with a progressively decreasing ability to excrete oxalate leading to a decline in kidney function. A proposed dissolving effect on systemic calcium oxalate deposits attributed to the novel compositions comprised in the drug products presented herein confer particularly beneficial effects to patients with hyperoxalemia having a reduced kidney function; said compositions enhancing excretion of oxalate from body fluids. There is also provided a manner to treat or prevent oxalate-related inflammation.

Hence, to at least mitigate some of the remaining problems in the art, it is hereby provided pharmaceutical compositions and enteric-coated capsules, as further described in the below.

In one aspect, there is provided a pharmaceutical composition comprising:
(i) about 10% to about 25% by dry weight of *Oxalobacter formigenes*,
(ii) about 50% to about 65% by dry weight of sucrose; and
(iii) about 10% to about 30% by dry weight of one or more cryopreserving agents and/or excipients.

Naturally, the compositions described herein may comprise some water, such as about 3% water.

In another aspect, there is provided an enteric-coated capsule for oral administration to a subject in need thereof comprising a pharmaceutical composition as defined herein, wherein said enteric-coated capsule is for targeted delivery of *Oxalobacter formigenes* to the small intestine and/or to the ileum of said subject.

There is also provided herein an enteric-coated capsule for oral administration to a subject, said capsule comprising *Oxalobacter formigenes* in an amount of about $10^9$ to about $10^{10}$ CFUs, and excipients and/or cryopreserving agents, wherein said enteric-coated capsule is targeted for delivery of *Oxalobacter formigenes* to the small intestine and/or to the ileum of said subject, said capsule showing essentially no disintegration within one hour of incubation in Simulated Gastric Fluid (SGF) having a pH of about 1.2±0.1 and comprising about 3.2 mg/ml of pepsin at a temperature of about 37° C., but wherein a start of disintegration of said capsule is detected after about one hour incubation in Simulated Intestinal Fluid (SIF) having a pH of about 6.8±0.1 and comprising about 10 mg/ml of pancreatin at about 37° C.

There is also provided a pharmaceutical composition as disclosed herein, or an enteric-coated capsule comprising a pharmaceutical composition as disclosed herein, for use as a medicament.

There is furthermore provided a use herein of the pharmaceutical composition or the enteric-coated capsules for treating and/or preventing an oxalate-related disorder, or more particularly calcium-oxalate deposition related disorder(s), such as calcium-oxalate deposition related disorder(s) involving hyperoxalemia; said composition increasing the excretion of oxalate from body fluids. There is also herein provided the use of the pharmaceutical composition or the enteric-coated capsules in treating and/or preventing oxalate-related inflammation.

The present disclosure is in a general aspect related to: hyperoxaluria, primary hyperoxaluria and secondary hyperoxaluria; but more specifically to hyperoxalemia, accumulation of oxalate in blood plasma, oxalosis associated with Chronic Kidney Disease (CKD) and end stage renal disease (ESRD) such as in Short Bowel Syndrome (SBS), bariatric surgery with jejunal/ileal resection or Roux-en-Y procedures, Zellweger's disease, cancers with jejunal/ileal resection, renal or other infections with *Aspergillus niger*; hyperoxalemia in ESRD-patients on dialysis and furthermore in some cases to oxalate-related inflammation, such as enteric hyperoxalemia, inflammation in the intestinal or tubular epithelium, cardiac conductance disorders, vulvodynia, idiopathic calcium oxalate kidney stone disease (urothiliasis), inflammatory bowel disease (IBS), Small Intestine Bacterial Overgrowth (SIBS), gastroenteritis, gastritis, enteritis, enterocolitis, ulcerative colitis, Crohn's disease, and an oxalate-related disorder in patients treated with a gastrointestinal lipase inhibitor.

A composition according to the present disclosure may be capable of slowing down, stopping or reversing disease progression and progression of hyperoxalemia and calcium oxalate deposition that leads to CKD.

A composition according to the present disclosure is furthermore capable of increasing oxalate excretion, e.g. urinary excretion of oxalate, thereby reducing systemic oxalate deposition.

There is also provided by the present disclosure a method for treating and/or preventing an oxalate-related disorder, or another disorder or disease state as described herein, said method comprising administering a pharmaceutically effective amount of a pharmaceutical composition as defined herein or an enteric-coated capsule as defined herein comprising a pharmaceutically effective amount of a pharmaceutical composition to a subject in need thereof.

There is furthermore provided a method for preparing a pharmaceutical composition, said method comprising the steps of:
a) mixing a cell paste of *Oxalobacter formigenes* with excipients and/or cryopreserving agents and optionally water; and
b) lyophilizing the composition obtained in step a).

There are also provided herein novel medical uses of a composition comprising *Oxalobacter formigenes* in light of the improved effects shown herein.

There is in addition provided herein a composition comprising *Oxalobacter formigenes* for use in the treatment and/or prevention of a calcium-oxalate deposition related disorder(s), such as calcium-oxalate deposition related disorder(s) involving hyperoxalemia, such as wherein said use is for the treatment and/or prevention of Chronic Kidney Disease (CKD).

There is also provided a composition comprising *Oxalobacter formigenes* for use in the treatment and/or prevention of oxalate-related inflammation.

DETAILED DESCRIPTION OF THE DISCLOSURE

Definitions

Figure 1:
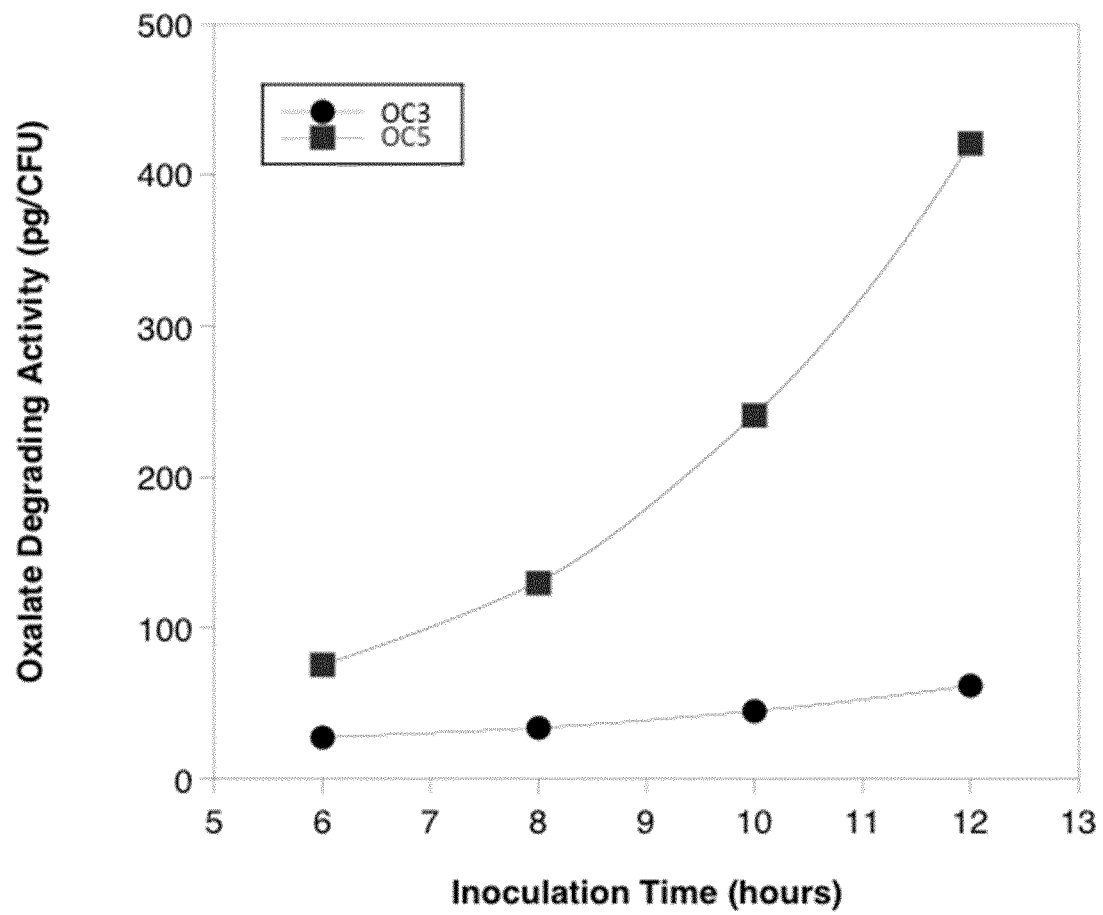
FIG. 1: Recovery from the lyophilized state of a presently disclosed, new pharmaceutical composition (OC5) and a previous composition (OC3).

All words and terms used herein shall be considered to have the same meaning usually given to them by the person skilled in the art, unless another meaning is apparent from the context.

The term "dry weight" as referred to herein, is intended to mean the weight of a composition wherein most of the water has been removed therefrom, such as by a drying process (e.g. lyophilisation).

The terms "cryopreserving agents" and "excipients" may sometimes be used interchangeably herein. However the term "cryopreserving agent" is herein intended to refer to an agent used to preserve cell viability when cooling to sub-zero temperatures. Cryopreservation is a process that is well-known in the art. Herein, the compositions also comprise one or more "excipients", which term is mainly used to describe other ingredients present in the composition, such as ingredients added thereto in order to, in other manners than cryopreservation, preserve stability or prevent degradation of the composition, as well as to absorb moisture. A purpose of an excipient can also be to achieve desired powder properties (e.g. free flowing powder).

An "enteric-coated" capsule as defined herein, refers to a capsule having outer surface coating characteristics, which makes it suitable for targeted delivery of a pharmaceutical agent, present therein, to a specific segment of an enteric part of the intestine. An enteric coating can also be described as a barrier applied on an oral drug preventing it from dissolution or disintegration in the gastro-intestinal environment. Accordingly, such a coating allows the drug to survive the acidic and enzymatic environment of the stomach and the duodenum. Herein, the term "capsule" may have any suitable form as long as it is encapsulating the pharmaceutical composition in a manner, which makes it suitable for transport and administration to the small intestine, such as the ileum, of a subject after the oral administration. Herein, an enteric-coated capsule is specifically targeted to the small intestine and/or to the ileum. This was proven to be particularly efficient in the present context.

Compositions "comprising" one or more recited elements may also include other elements not specifically recited.

The singular "a" and "an" shall be construed as including also the plural.

DETAILED DESCRIPTION

According to the present disclosure, there is provided herein an improved pharmaceutical composition; a composition comprising *Oxalobacter formigenes* as well as a drug product in the form of an enteric-coated capsule comprising said pharmaceutical composition having an improved effect on oxalate-related disorders, and particularly on calcium-oxalate deposition related disorder(s), such as calcium-oxalate deposition related disorder(s) involving hyperoxalemia. Hyperoxalemia is characterized by high levels of oxalate in the plasma e.g. leading to the formation and deposition of calcium oxalate complexes in the body. It has been shown difficult in the art to identify pharmaceutical compositions that have an effect on the formed calcium oxalate deposits per se and/or upon hyperoxalemia. If such an effect is possible to achieve, it may aid in delaying or stopping formation of said oxalate deposits or aid in the dissolution of said oxalate deposits and eventually possibly also to a reversal of a disorder associated therewith, such as kidney function disorders. Such an effect is noted herein for a composition according to the disclosure which is further described in the below.

Notably, herein, the terms "oxalate crystal deposits", "oxalate deposits", "deposits" or the like, are interchangeable with, or at least related to, the terms "calcium-oxalate deposits" and "calcium oxalate complexes" which are also used herein.

Hence, there is envisaged herein a use of said pharmaceutical composition particularly in the treatment of a disorder involving elevated levels of plasma oxalate, frequent systemic oxalate crystal deposits and a reduced kidney function. As it may take time to excrete dissolved oxalate deposits following treatment with *O. formigenes*, treatment periods of several months to several years are envisaged for subjects suffering from such disorders.

As further presented in the below, by performing a thorough clinical study the applicant has shown an improved effect in the form of an increased urinary oxalate excretion effect and also in relation thereto more specific medical uses of a pharmaceutical composition comprising *O. formigenes* as defined herein. Furthermore, a drug vehicle in the form of an enteric-coated capsule was shown to provide even further advantages to a final drug product encompassing said pharmaceutical composition, when said capsule is targeted to a particular part of the intestine as further explained herein. The drug product used in the clinical study, named OC5, is representative of the pharmaceutical composition and the enteric-coated capsule defined herein. Hence variations thereof, as presented in the following disclosure, are also encompassed by the disclosure.

The improved pharmaceutical composition comprised in OC5 and used in the clinical study performed comprises highly concentrated dried (e.g. lyophilized) bacteria of *O. formigenes* having a fast recovery time, a minimum viable cell count of Not Less Than (NLT) $10^9$ CFU/capsule (such as about $10^9$ to $10^{10}$ CFU/capsule, and an oxalate reducing capacity of NLT of about 100 mmol oxalate/capsule/19 hours, such as about 200 mmol, about 300 mmol, about 400 mmol, about 500 mmol, or even up to about 2 mol oxalate/capsule/19 hours, or the like. The pharmaceutical composition is presented in an enteric-coated capsule for oral administration, particularly formulated for targeted delivery to the small intestine and/or to the ileum. This was shown herein to be a particularly useful site for action of *O. formigenes*. Such a combination was particularly useful for obtaining the effects disclosed herein.

Surprisingly, the treatment with the herein presented composition, OC5, did not reduce, but instead increased the urinary oxalate excretion in treated patients, thus suggesting dissolution of oxalate deposits in the patients, which in turn suggests a highly efficient composition for treating oxalate-deposition-related disorders as more specifically defined herein. *O. formigenes* was successfully delivered to the gastrointestinal tract, and more particularly to the small intestine and/or to the ileum, and was well tolerated by the subjects that received the composition. Analyses discussed herein showed a statistically significant increase in urinary oxalate normalised to creatinine for the group obtaining the composition (Table 4), and even more importantly, it also showed an increased urinary calcium excretion (Table 14), a reduced blood urea nitrogen (Table 9), a reduced urinary volume (Table 10) and an increased urinary citrate excretion (data not shown). These are all markers for increased excretion of calcium oxalate deposits and a stopped progression of kidney deterioration. Hence, the present composition is envisaged for such a purpose, and also a composition comprising Oxalobacter formigenes, for a novel medical use.

In a previous open-label study (Hoppe et al., 2006), administration of an alternative composition, named OC3, led to a statistically significant reduction in urinary oxalate excretion over 4 weeks in almost all patients, and there were no safety concerns. However, a subsequent larger, double blind trial with a modified formulation, another alternative composition, e.g. comprising a lower concentration of O. formigenes than the pharmaceutical composition disclosed herein, demonstrated no effect on urinary oxalate excretion [Hoppe et al., 2011] over 24 weeks. To improve the efficacy of a composition comprising O. formigenes and to overcome the issues with low activity and long recovery time and drug delivery for the previous formulations, improvements were made which resulted in the pharmaceutical composition presented herein.

The improved pharmaceutical composition comprised in this drug product has now been the subject of a placebo-controlled clinical trial illustrating the effects thereof which were shown to be particularly useful in the context of oxalate-related disorders, or more particularly calcium-oxalate deposition related disorder(s), such as calcium-oxalate deposition related disorder(s) involving hyperoxalemia.

Analysis of the clinical trial surprisingly showed a statistically significant increase in urinary oxalate excretion normalized to urinary creatinine excretion in the group treated with the novel active formulation (drug (OC5)) versus the group treated with placebo (Table 4).

As mentioned in the Results section, there was a negative correlation between baseline eGFR (estimated Glomerular Filtration Rate, a measure of kidney function) and plasma oxalate concentration (p=0.007) at baseline for all patients, which demonstrates that plasma oxalate is progressively increasing as eGFR is decreasing. eGFR is highly clinically relevant and plasma oxalate would therefore be a good indicator of PH disease progression. In a recent publication, eGFR at diagnosis was shown to be associated with incident ESRD in PH patients [Zhao et al., 2016]. In PH progression, the kidney deterioration rate is related to the time for exposure to high oxalate (age) and seems to be accelerating with declining eGFR. In parallel, plasma oxalate and calcium oxalate deposition gradually increase.

In the subgroup analysis, which is explained further in the experimental section, the most notable differences between OC5- and placebo-treated patients were observed in subgroups of older patients (≥18 years) and patients with reduced kidney function (<90 mL/min/1.73 m²). That these two subgroups were similar was unsurprising given that they have both been exposed to high oxalate for a long time and in consequence built up calcium oxalate deposits that cause reduced kidney function.

Importantly, the treatment with the pharmaceutical composition appeared to have a more marked effect in those patients with more advanced PH. The difference was the opposite of what was expected; instead of a decrease in the urinary oxalate excretion, administration of the composition actually led to an increase in excretion. This is a highly relevant finding, opening up for improved treatments of oxalate-related disorders with hyperoxalemia suffering from calcium oxalate deposition by using a composition according to the present disclosure.

O. formigenes can be of genotype 1 or genotype 2; both types are naturally occurring. OC5 comprises O. formigenes genotype 1. A statistically significant negative correlation between change in plasma oxalate concentration and change in the number of O. formigenes genotype 1 in the active group (i.e. the group receiving OC5) suggests that the introduced O. formigenes bacteria are able to metabolise free oxalate that originates from plasma (Table 8). O. formigenes genotype 2, which was present in 3 patients each in the active and placebo groups at baseline, increased only in the active group. O. formigenes genotype 2 did not increase in the placebo group, which indicates that the drug transports excess oxalate from plasma to the intestine i.e. it is activating the active transport. These findings support that the herein presented pharmaceutical composition in the form of OC5 is creating an active flux of oxalate from plasma to the intestine.

Parallels can be drawn to patients with gout in the sense that just as patients with PH have increased plasma oxalate concentration, patients with gout have increased plasma urate concentration. In time, this leads to deposition of monosodium urate crystals in joints. It has been reported that uric acid-lowering treatment of gout disrupts the equilibrium between plasma urate and urate crystals, which then gradually dissolve over 3-33 months [Pascual and Sivera, 2007].

Calcification of soft tissue mediated by calcium phosphate deposition is a common problem in Chronic Kidney Disease patients. Several approaches are available to reduce either calcium or phosphate, both approaches successfully leading to increased excretion and dissolution of calcium phosphate deposits.

Similarly, in the OC5-treated patients, the O. formigenes promotes active elimination of oxalate, mediating transfer of free oxalate from plasma to the gut. This process disrupts the equilibrium between free plasma oxalate, protein-associated oxalate and deposited calcium oxalate. The disruption in equilibrium may drive towards free oxalate and lead to a dissolution of deposited calcium oxalate crystals. As crystal dissolution is controlled by the surrounding bulk concentration of the respective counter ion, crystals may dissolve momentarily under saturation concentration and pulse increased oxalate in plasma and urine as a consequence of dissolution.

Since calcium oxalate deposits are expected to be more pronounced in patients with reduced renal function, this may explain why the effect of OC5 treatment was greater in patients with more advanced kidney disease (eGFR<90 mL/min/1.73 m²). The increased urine calcium excretion in patients with eGFR<90 mL/min/1.73 m² adds further weight to the theory of dissolution of calcium oxalate crystals.

Hence, it is herein proposed a direct effect on the calcium oxalate deposits per se, achieving a dissolution thereof which provides an efficient tool for enhancing removal of systemic calcium oxalate deposits in the treatment of disorders associated with the deposition of calcium oxalate in the body, and even in the reversal of or at least stopping of the progression of such a disorder.

Further analyses also indicated that OC5 treatment resulted in additional benefits of use in clinical practice; reduced BUN and decreased urine output in the OC5 group suggested that renal water reabsorption and urine-concentrating ability, both hallmarks for kidney deterioration, were improving in these patients (Table 9 and Table 10). The recent publication from Zhao et al., 2016, concludes that urinary volume is generally increased in PH-patients, and that urinary volume at the time of diagnosis correlates negatively with the eGFR (p=0.001). The authors suggest that the increased urinary volumes reflect decreased urinary-concentrating abilities and dehydration among PH-patients who have established tubulointerstitial injury. These observations support the findings presented herein where reduced urinary volume was seen after OC5 treatment and would thus indicate a beneficial treatment effect for the kidney. Blood urea nitrogen (BUN), being a marker for tubular injury, is highly elevated in PH-patients. The finding that OC5 treatment tended to reduce BUN and reduce urinary volume could indicate improved urine-concentrating ability and reduced dehydration, a beneficial treatment effect, e.g. for the kidney. It is surprising that such effect was shown already after only 8 weeks treatment, kidney deterioration having progressed for years.

Calcium oxalate crystals are known to cause inflammatory responses (Worcester et al., 2013). The significant decrease of eosinophils and the tendency for leukocyte and lymphocyte counts to decrease in the OC5-treated patients and increase in placebo-treated patients over 8 weeks (as shown in the Results section) indicated that *O. formigenes* treatment, by potentially reducing calcium oxalate crystals, may also have had a beneficial effect on PH-associated inflammation (Tables 9 and 11). Accordingly, there is presented herein a further medical use of the pharmaceutical composition as defined herein for oxalate-related inflammation, which may be a result of secondary hyperoxaluria.

Oxalate crystal-related inflammation occurs in all soft tissue exposed to said crystals including the kidney and the heart. In the kidney, inflammation causes phagocytosis of crystals and internalization of deposits in cells (nephrocalcinosis). In the heart, inflammation causes internalization of deposits in the myocardium, resulting in stiffness and reduced contractibility of the heart.

Treatment with the pharmaceutical composition also significantly increased the number of *O. formigenes* cells in the gut and was well tolerated (Table 5). In contrast to pre-study expectations, the treatment significantly increased urinary oxalate per creatinine excretion.

Expectations were that *Oxalobacter* would metabolise free oxalate and thus decrease the oxalate burden in the body, causing a lower excretion. This hypothesis relied on the assumption that calcium oxalate deposits were insoluble. On the contrary, *Oxalobacter* increased the excretion of oxalate presumably through dissolution of crystals and possibly also through increasing the activity of transporter proteins in intestinal and tubular epithelium.

Results of the analysis were consistent with a new hypothesis that *O. formigenes* promoted active elimination of oxalate from plasma, to the ileum (intestine), and subsequently perturbed the equilibrium between free plasma oxalate, protein-associated oxalate and deposited calcium oxalate. This led to increased dissolution of calcium oxalate deposits and subsequently increased (urinary) oxalate excretion. As plasma oxalate is gradually increasing in PH-patients, this hypothesis suggests that, in line with the gout model, a stabilisation or a reduction in plasma oxalate concentration over time versus placebo would be the preferred metric for the effectiveness of OC5 treatment.

As a result of the outcome of the clinical studies, it is proposed herein an improved pharmaceutical composition comprising *Oxalobacter formigenes*, as well as an enteric-coated capsule comprising said pharmaceutical composition.

Accordingly, there is provided herein a pharmaceutical composition comprising:
(i) about 10% to about 25% by dry weight of *Oxalobacter formigenes*,
(ii) about 50% to about 65% by dry weight of sucrose; and
(iii) about 10% to about 30% by dry weight of one or more cryopreserving agents and/or excipients.

Naturally, said pharmaceutical composition may also comprise water, such as in an amount of about 1-5%, such as about 3%.

A pharmaceutical composition may also consist of the above described ingredients and optionally water.

The contents of the pharmaceutical compositions mentioned herein are described in percentages and in dry weight. This dry composition has been obtained through a drying-process, such as freeze-drying, and may in such a context also be referred to as a powder composition or a lyophilized/freeze-dried (powder) composition. When drying a composition, there may be some water left which is illustrated by the compositions comprising a certain amount of water.

More specifically, there is provided a pharmaceutical composition comprising about 10% to about 20%, about 10% to about 25%, about 15% to about 20%, about 15% to about 25%, about 17% to about 21%, about 18% to about 22%, or about 18% to about 20%, such as about 15%, 16%, 17%, 18%, 19%, 20%, 21% or 22% by dry weight of *Oxalobacter formigenes* in said composition. The amounts of *Oxalobacter formigenes* may also vary slightly (mainly towards a higher percentage), or be as further exemplified herein. As pointed out, the herein disclosed pharmaceutical composition comprises a high, suitable, concentration of bacteria. The higher concentration of bacteria provides for an improved effect or recovery rate for the composition, as further illustrated herein.

Figure 2:
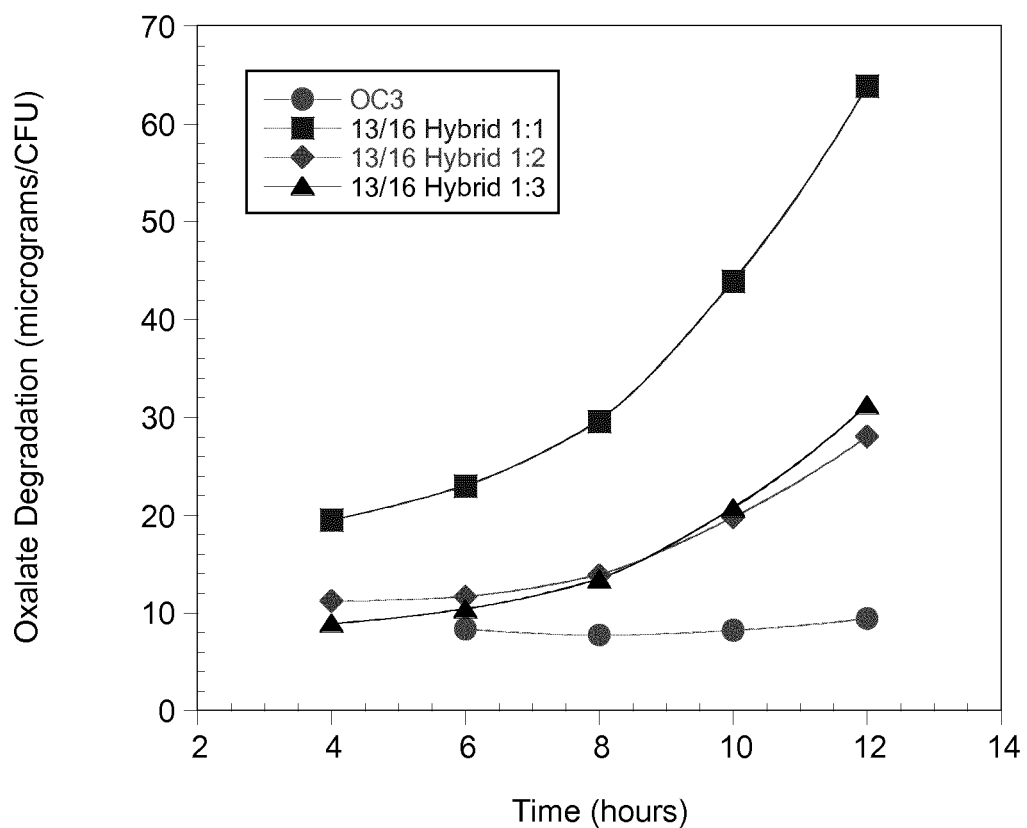
FIG. 2: Oxalate degrading activity of a previous composition (OC3) as compared to the new pharmaceutical composition (OC5). Potency is represented as the amount of oxalate degraded per CFU. The different hybrid formulations all contain sucrose while the OC3 formulation does not.

Furthermore, a pharmaceutical composition herein may comprise about 50% to about 65% by dry weight of sucrose, such as about 52% to about 62%, about 54% to about 60%, or about 56% to about 58%, such as about 54%, 55%, 56%, 57%, 58%, 59%, 60%, 61%, 62%, 63%, 64% or 65%. The amounts may also vary slightly, or may be as further exemplified herein. The usage of sucrose in the pharmaceutical composition was proven to present a good alternative to other disaccharides, as it provides for an increased stability of the composition. The combination of a high concentration of *Oxalobacter formigenes* and sucrose as the main excipient of the pharmaceutical composition was proven to be a successful combination to achieve an improved medical effect presented herein. The improved recovery and oxalate degrading activity of a composition comprising sucrose as a main excipient is also shown in FIG. 2. The hybrid compositions represent different percentages of sucrose content, illustrating the improved compositions. Hybrid 1:1 comprises the highest amount of sucrose (Hybrid: cell paste: excipient solution including sucrose).

The amount(s) of one or more cryopreserving agents and/or excipients may be about 10% to about 30% by dry weight, such as about 15%, 16%, 17%, 18%, 19%, 20%, 21%, 22%, 23%, 24%, 25%, 26%, 27%, 28%, 29% or 30% of one or more cryopreserving agents and/or excipients.

Notably, all % amounts mentioned herein may generally at least vary about 1-3%, i.e. ±1-3% depending on the exact manufacturing process and cell density used for preparing the pharmaceutical composition. The compositions are prepared from a cell paste and excipients in solution and then frozen and lyophilized by procedures known in the art.

In a pharmaceutical composition presented herein, the excipients and/or cryopreserving agents in (iii) may be selected from the group consisting of maltodextrin, oligofructose and alginate. Other, equally functional and structurally similar agents may also be used.

In a pharmaceutical composition as disclosed herein, about 15% to about 21%, such as about 16% to about 19%, such as about 15%, 16%, 17%, 18% or 19% by dry weight of maltodextrin may be used.

There is further provided herein a pharmaceutical composition comprising:
i) about 1% to about 5% by dry weight of oligofructose; and
ii) about 0.5% to about 2% by dry weight of alginate. Said pharmaceutical composition may also comprise water, such as in the amount of about 1% to about 5% by weight of said composition.

A pharmaceutical composition as presented herein may also comprise about 0.5% to about 1.5% by dry weight of alginate, or an agent similar to alginate, such as about 1%. Oligofructose may be about 1%, 2%, 3%, 4% or 5% by dry weight.

There is further provided herein a pharmaceutical composition comprising:
about 17% to about 22% by dry weight of *Oxalobacter formigenes*,
about 52% to about 62% by dry weight of sucrose;
about 17% to about 25% by dry weight of one or more cryopreserving agents and/or excipients.

Furthermore, there is provided a pharmaceutical composition comprising:
about 19% by dry weight of *Oxalobacter formigenes*,
about 57% by dry weight of sucrose;
about 21% by dry weight of one or more cryopreserving agents and/or excipients, and remaining water. The cryopreserving agents and/or excipients may be alginate, maltodextrin and/or oligofructose, and may be present in the amounts of about 1% alginate, about 17% maltodextrin and about 3% oligofructose by dry weight.

Another aspect of the present disclosure provides an enteric-coated capsule for oral administration to a subject in need thereof, wherein said capsule comprises a pharmaceutical composition as defined herein. There is further provided a capsule, which comprises the structural coating characteristics to target the delivery of *Oxalobacter formigenes* to the small intestine, or more particularly to the small intestine and/or to the ileum, of said subject. An advantageous medical effect has been shown by targeting the delivery of *Oxalobacter formigenes* to these parts of the small intestine.

The structural characteristics of the enteric-coated capsule used may be described in a functional manner by e.g. referring to its ability to withstand disintegration in in vitro conditions simulating conditions in the gastrointestinal part of the body. Herein, the capsule is described both with regard to its ability to withstand disintegration in the stomach environment, and with regard to its ability to withstand disintegration for a limited period of time also in an intestinal environment. Hence, herein, the characteristics of the enteric-coated capsule are mainly described in relation to its ability to withstand disintegration during incubation in "Simulated Gastric Fluid" (SGF) and in "Simulated Intestinal Fluid" (SIF).

"Simulated Gastric Fluid" (SGF) is an artificial dissolution medium that is intended to represent stomach acid. It may prepared by dissolving sodium chloride and subsequently adding purified pepsin (e.g. derived from porcine stomach mucosa, with an activity of about 800 to 2500 units per mg of protein), in hydrochloric acid. The test solution has a pH of about 1.2±0.1. The temperature of the SGF is kept at about 37° C. and the concentration of the enzyme in the fluid is about 3.2 mg/ml.

"Simulated Intestinal Fluid" (SIF) is an artificial dissolution medium that is intended to represent intestinal fluid. It may prepared by dissolving potassium phosphate in water and adding sodium hydroxide and adjusting the pH to pH 6.8±0.1 and subsequently adding purified pancreatin. The temperature of the SIF is kept at about 37° C. and the concentration of the enzyme in the fluid is about 10 mg/ml.

Six capsules may be tested at the same time. Complete disintegration is defined as that state in which any residue of the unit, except fragments of insoluble coating or capsule shell, remain on the screen of the test apparatus or adhere to the lower surface of the discs, is a soft mass having no palpably firm core. The acceptance criterion for SGF is met if all six capsules show no evidence of disintegration or rupture permitting the escape of contents. The acceptance criteria for SIF are met if all six capsules show evidence of a start of disintegration within 60 minutes. A procedure for disintegration of tablets and capsules is also described in the European Pharmacopoeia 5.0, 2.9.1 (Test A).

In accordance therewith, the enteric-coated capsule can be defined as showing essentially no disintegration within one hour of incubation in Simulated Gastric Fluid (SGF) having a pH of about 1.2±0.1 and comprising about 3.2 mg/ml of pepsin at a temperature of about 37° C., but wherein a start of disintegration of said capsule is detected within about one hour in Simulated Intestinal Fluid (SIF) having a pH of about 6.8±0.1 and comprising about 10 mg/ml of pancreatin at about 37° C. These characteristics of the enteric-coated capsule explains that it will survive the acidic environment in the stomach, and it will also last for some time in the intestinal environment, thereby efficiently targeting delivery of *Oxalobacter* to the small intestine and/or to the ileum. This was shown to be the most efficient target for delivery and start of release of this pharmaceutical composition. Herein, it is also shown that the disintegration definition in vitro indeed corresponds to an in vivo disintegration in the small intestine and/or to the upper part of the large intestine in a clinical subject. This is visualized e.g. in FIG. 3.

Notably, a capsule herein, having the characteristics of a start of disintegration within about one hour in Simulated Intestinal Fluid (SIF) having a pH of about 6.8±0.1 and comprising about 10 mg/ml of pancreatin at about 37° C., was proven particularly useful. Hence, this means that the capsule remains for quite some time in the intestinal tract, resulting in a slow release of the pharmaceutical composition. This is a difference compared to other capsules, e.g. where a complete disintegration (or collapse) is seen within about one hour in Simulated Intestinal Fluid (SIF) having a pH of about 6.8±0.1 and comprising about 10 mg/ml of pancreatin at about 37° C. As previously mentioned herein, the capsule may be a gelatin capsule, such as a hard gelatin capsule, or another similar capsule providing similar characteristics, thus resulting in a preferred release profile of the drug.

Examples of polymer coatings that may be used to prepare a coating for a capsule comprising a pharmaceutical composition according to the present disclosure that withstands disintegration within the above defined limits are e.g. methacrylic acid polymers including methacrylic acid copolymers and anionic methacrylic acid copolymers such as provided by the coatings of Eudragit®. These may e.g. be purchased from Evonik Industries and may also be prepared by a person skilled in the art, further optionally taking into account additional available information available to the skilled person, such as Remington's Pharmaceutical Sciences. The selection of the appropriate polymers to produce or coat a capsule may be performed by the skilled person by taking into account the particulars presented herein regarding the targeting of the capsules to the small intestine and/or to the ileum.

The capsule may be a gelatin capsule, such as a hard gelatin capsule, or another similar capsule providing similar characteristics.

There is also provided an enteric-coated capsule as disclosed herein, wherein said capsule comprises *Oxalobacter formigenes* in an amount of about $10^9$ to about $10^{10}$ CFUs (Colony Forming Units). The amount of *Oxalobacter formigenes* can also be higher, but the mentioned amount per capsule has been shown to function particularly well in the context of the present composition with regards to the effect associated therewith and it also renders preparation of the composition more efficient. Examples of higher amounts per capsule is $10^{11}$, $10^{12}$, $10^{13}$, $10^{14}$ and $10^{15}$ CFUs/capsule.

There is also provided an enteric-coated capsule wherein the oxalate-degrading activity in vitro of the *Oxalobacter formigenes* when present in said enteric-coated capsule is no less than (NLT) about 100 mmol/capsule/19 hours, such as about 200 mmol, about 300 mmol, about 400 mmol, about 500 mmol or even up to about 2 moles, as previously mentioned herein. Instead of per capsule it may also be referred to as per dose. This defines the activity of the bacteria selected for the preparation of the pharmaceutical composition, i.e. it allows disregarding certain batches of cells, which may contain less active cells when preparing the composition. It was shown herein to be possible to obtain a very efficient pharmaceutical product by using bacteria possessing such an oxalate degrading activity. The identification of bacteria possessing such characteristics may be performed in an assay measuring oxalate degrading activity as illustrated in the experimental section.

The potency (oxalate degrading activity) of the new pharmaceutical composition is also illustrated in FIG. 1, showing that the novel composition begins replicating much quicker than the previous formulation used. This illustrates the improved characteristics of the present composition.

There is furthermore provided herein an enteric-coated capsule for oral administration to a subject, said capsule comprising *Oxalobacter formigenes* in an amount of about $10^9$ to about $10^{10}$ CFUs, and excipients and/or cryopreserving agents, wherein said enteric-coated capsule is targeted for delivery of *Oxalobacter formigenes* to the small intestine and/or to the ileum of said subject. There is furthermore provided this capsule when showing essentially no disintegration within one hour of incubation in Simulated Gastric Fluid (SGF) having a pH of about 1.2±0.1 and comprising about 3.2 mg/ml of pepsin at a temperature of about 37° C., but wherein a start of disintegration of said capsule is detected within about one hour in Simulated Intestinal Fluid (SIF) having a pH of about 6.8±0.1 and comprising about 10 mg/ml of pancreatin at about 37° C. The oxalate-degrading activity in vitro of the *Oxalobacter formigenes*, when present in said capsule, may be no less than (NLT) about 100 mmoles/capsule/19 hours, or as previously defined herein. Examples of capsules and polymer coatings are provided herein.

There is furthermore provided a pharmaceutical composition as defined herein, or an enteric-coated capsule, for use as a medicament. Said use may be for the treatment and/or prevention of an oxalate-related disorder, or more particularly calcium-oxalate deposition related disorder(s), such as calcium-oxalate deposition related disorder(s) involving hyperoxalemia.

Herein, whenever it is referred to a medical use of said pharmaceutical composition or of said enteric-coated capsule, this is also intended to refer to the use thereof in the manufacture of a medicament for the treatment or prevention of a medical condition mentioned herein.

There is also provided a pharmaceutical composition or an enteric-coated capsule for use in the treatment and/or prevention of an oxalate-related disorder, wherein said disorder is selected from the group consisting of hyperoxaluria, primary hyperoxaluria and secondary hyperoxaluria.

There is also herein provided the use of a pharmaceutical composition or an enteric-coated capsule for treating and/or preventing oxalate-related inflammation.

The present disclosure is related to hyperoxaluria, primary hyperoxaluria and secondary hyperoxaluria. In a further context, it is directed to hyperoxalemia, accumulation of oxalate in blood plasma, oxalosis associated with Chronic Kidney Disease (CKD) and end stage renal disease (ESRD) such as in Short Bowel Syndrome (SBS), bariatric surgery with jejunal/ileal resection or Roux-en-Y procedures, Zellweger's disease, cancers with jejunal/ileal resection, renal infections with *Aspergillus niger*, and ESRD-patients on dialysis. It is further directed to enteric hyperoxaluria, inflammation in the intestinal or tubular epithelium, cardiac conductance disorders, vulvodynia, idiopathic calcium oxalate kidney stone disease (urothiliasis), inflammatory bowel disease (IBS), Small Intestine Bacterial Overgrowth (SIBS), gastroenteritis, gastritis, enteritis, enterocolitis, ulcerative colitis, Crohn's disease, and an oxalate-related disorder in patients treated with a gastrointestinal lipase inhibitor.

In a further aspect, there is also provided herein *Oxalobacter formigenes* for use in the treatment and/or prevention of oxalate-related inflammation.

The pharmaceutical composition or the enteric-coated capsule defined herein may be administered in amounts containing about $10^9$ to about $10^{10}$ CFUs of *O. formigenes* at least twice a day for a continuous period of time, such as a period lasting for at least months or years, to a subject in need thereof. Such a period may last from 1, 2, 3, 4, 5, 6 or up to 12 months, 1, 2, 3, 4, or 5 or even more years, until the progression of increased levels of plasma oxalate have been slowed down, stopped or lowered and maintained at a healthier, lower level, such as at 1-3 μmol/L.

As previously mentioned herein, the present composition is particularly useful for the treatment and/or prevention of an oxalate-related disorder associated with hyperoxalemia and the formation of systemic calcium oxalate deposits.

There is also herein provided the use of the pharmaceutical composition or the enteric-coated capsules in treating and/or preventing oxalate-related inflammation.

There is furthermore provided a method for treating and/or preventing an oxalate-related disorder or more particularly a calcium-oxalate deposition related disorder(s), such as calcium-oxalate deposition related disorder(s) involving hyperoxalemia, said method comprising administering a pharmaceutically effective amount of a pharmaceutical composition as defined herein or an enteric-coated capsule as defined herein comprising a pharmaceutically effective amount of a pharmaceutical composition as defined herein to a subject in need thereof.

Said subject may be a mammal, such as a human.

Said method comprises treating and/or preventing hyperoxaluria with hyperoxalemia, primary hyperoxaluria and secondary hyperoxaluria. Said method further relates to the treatment and/or prevention of hyperoxalemia, accumulation of oxalate in blood plasma, oxalosis associated with Chronic Kidney Disease (CKD) and end stage renal disease (ESRD) such as in Short Bowel Syndrome (SBS), bariatric surgery with jejunal/ileal resection or Roux-en-Y procedures, Zellweger's disease, cancers with jejunal/ileal resection, renal infections with *Aspergillus niger*, ESRD-patients on dialysis. The method further pertains to oxalate-related inflammation, and more particularly the treatment and/or prevention of enteric inflammation from hyperoxaluria, inflammation in the intestinal or tubular epithelium, cardiac conductance disorders, vulvodynia, idiopathic calcium oxalate kidney stone disease (urothiliasis), inflammatory bowel disease (IBS), Small Intestine Bacterial Overgrowth (SIBS), gastroenteritis, gastritis, enteritis, enterocolitis, ulcerative colitis, Crohn's disease, and an oxalate-related disorder in a patient treated with a gastrointestinal lipase inhibitor.

Said method is also directed to further increase systemic oxalate excretion when said composition is administered to a subject in need thereof. A subject in need thereof is identified herein as suffering from one or more of the disorders of the disclosure.

There is also provided a method, wherein said pharmaceutically effective amount comprises *Oxalobacter formigenes* in an amount of about $10^9$ to about $10^{10}$ CFUs at least twice a day for a continuous period of time, such as a period lasting for at least months or years to a subject in need thereof. Such a period may last from 1, 2, 3, 4, 5, 6 or up to 12 months, 1, 2, 3, 4, or 5 or even more years, until the levels of plasma oxalate have been lowered, and are maintained at a healthier, lower level, such as at 1-3 µmol/L.

There is also provided a method for preparing a pharmaceutical composition as defined herein, said method comprising the steps of:

a) mixing a cell paste of *Oxalobacter formigenes* with excipients and/or cryopreserving agents and optionally water; and b) lyophilizing the composition obtained in step a).

In other aspects, the following is provided herein:

There is also provided *Oxalobacter formigenes* for use in the treatment and/or prevention of renal infections with *Aspergillus niger*.

There is also provided herein *Oxalobacter formigenes* for use in the treatment and/or prevention of a calcium-oxalate deposition related disorder(s), such as a calcium-oxalate deposition related disorder(s) involving hyperoxalemia, as more specifically defined herein in other contexts.

There is also provided herein *Oxalobacter formigenes* for use in the treatment and/or prevention of Chronic Kidney Disease (CKD).

There is also provided herein *Oxalobacter formigenes* for use in the treatment and/or prevention of oxalate-related inflammation, as more specifically defined herein in other contexts.

*Oxalobacter formigenes* is provided in a pharmaceutical composition in a therapeutically effective amount thereof, as exemplified herein.

The present disclosure will now be illustrated by the following experimental section, but it is not intended to be limited thereto.

EXPERIMENTAL SECTION

Content, Activity and Disintegration of the Novel Formulation

Oxalate-Degrading Activity

Testing of the potency, i.e. the oxalate degrading activity of *O. formigenes*, is performed indirectly by measuring the amount of formate generated from oxalate degradation activity during culture of cells in oxalate containing media (60 mM oxalate "OxB" medium, Allison et al., 1985, Medium B). Samples are withdrawn and filtered, after incubation at 37° C. The concentration of formate is determined by High Performance Liquid Chromatography (HPLC) against a formate standard curve using a cation exchange column. Stoichiometrically, one mole of formate is generated for each mole of oxalate consumed (Steward et al., 2004):

$$\text{Oxalate} \rightarrow \text{oxalyl-CoA} \rightarrow \text{formyl-CoA} + CO_2 \rightarrow \text{formate}$$

The assay for the present formulation, e.g. OC5, measures accumulated oxalate degradation at about 19 hours, a time point where linearity between sample dilutions is observed and the cells have reached exponential phase.

By this route, the assay is allowed to discriminate active oxalate degrading activity from background metabolic activity.

The graph in FIG. 1 reveals that the pharmaceutical composition of the present invention begins replicating much quicker than a previously used material. Since the *O. formigenes* cells have a limited time to recover and start degrading oxalate in vivo once the capsule has disintegrated, a short recovery time of the cells is important. If the recovery is not quick enough, the cells will have passed through the gastrointestinal tract before they have had the chance to exert their effect. Therefore, it is preferred to use a material having the particular growth rate and oxalate degrading activity as disclosed herein to achieve the improved pharmaceutical formulation.

Accordingly, the improved pharmaceutical formulation resulted in i) a faster recovery of the lyophilized powder (of OC5) compared to previous product lyophilized powder, as defined by the in vitro oxalate degrading activity measurement described above and ii) a higher viable cell count concentration. The oxalate degrading activity per dose of product is approximately 100 times higher in the present composition.

The present formulation is also more concentrated (as presented herein) than previous substances.

Therefore, both the total and the viable cell counts are higher per gram of material.

TABLE 1

Contents of lyophilized powder in OC3 and OC5 formulations

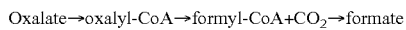

| | Lyophilised powder | |
| --- | --- | --- |
| | OC5 | OC3 |
| Cell paste | 19% | 1% |
| Oligofructose | 3% | 31% |
| Maltodextrin | 17% | 58% |
| Alginate | 1% | 4% |
| Trehalose | NA | 3% |
| Sucrose | 57% | NA |
| Water | 3% | 3% |

The contents listed in the above table are approximate, and may be varied within the ranges exemplified herein. One of the differences between the old and the new formulations is the excipient sucrose. The recovery traces in FIG. 2 shows recovery rates for different formulations containing sucrose while the OC3 formulation does not (i.e. FIG. 2 shows improved recovery and oxalate degradation for hybrid formulations compared to OC3).

Disintegration of OC5 Capsules Coated with Polymers

The target site for release of the pharmaceutical composition presented herein, and exemplified by OC5, is in the small intestine, in particular a preferred start of release of *Oxalobacter* in the formulation is targeted after duodenum, to jejunum or ileum, since the physical site for flux of oxalate into the intestinal lumen has been found to occur in the ileum as well as in the caecum and distal colon (Hatch and Freel, 2008, 2013).

The OC5 lyophilized powder contains the *O. formigenes* cells with fast growth characteristics. In developing OC5 it was decided to use enteric-coated capsules for targeted release of the bacteria, with the particulars presented in the below. The OC5 capsule may comprise a coating of Eudragit polymers FS30D and L30D55, but a composition presented herein is not limited thereto.

TABLE 2

Description of OC5 Capsules

| Drug Product | Capsule | Oxalate degrading activity per dose | Content per dose (CFU*) | Disintegration Time Specification for the OC5 capsule |
|---|---|---|---|---|
| OC5 | Size 4 enteric coated hard capsule | ≥100 mmol/dose, 19 h | $10^9$-$10^{10}$ | No evidence of disintegration within the first hour in SGF; Evidence of start disintegration within the first hour in SIF |

*CFU; colony forming units

Evaluation of OC5 Capsules Coated with Polymers In Vivo

The aim was to evaluate the in vivo behaviour of an enteric-coated capsule formulated to disintegrate in the small intestine. The capsules were coated with polymers and are designed to withstand an hour in simulated gastric fluid (SGF) and to show signs of capsule break-up within an hour in simulated intestinal fluid (SIF).

The disintegration process and transit of the capsules through the gastrointestinal tract is characterised using a scintigraphic method. The technique of gamma scintigraphy has become an increasingly useful tool in evaluating the in vivo performance of pharmaceutical dosage forms. Scintigraphy is non-invasive and provides information on deposition, dispersion and movement of the formulation. The radioactive load is minimal and all procedures are well established and generally considered safe.

A scintigraphic study to evaluate the in vivo behaviour of targeted enteric-coated capsules in male human volunteers was performed. The capsule, designed to disintegrate within 1 h in SIF, started to disintegrate at a mean time of 91.6±30.6 min after gastric emptying in vivo. Based on scintigraphic images obtained and evaluation of gastrointestinal transit times, it can be summarised that the majority of capsules started release in the small intestine, specifically in the ileum. A product capable of releasing *Oxalobacter* in the ileum has hence herein for the first time been developed.

Figure 3:
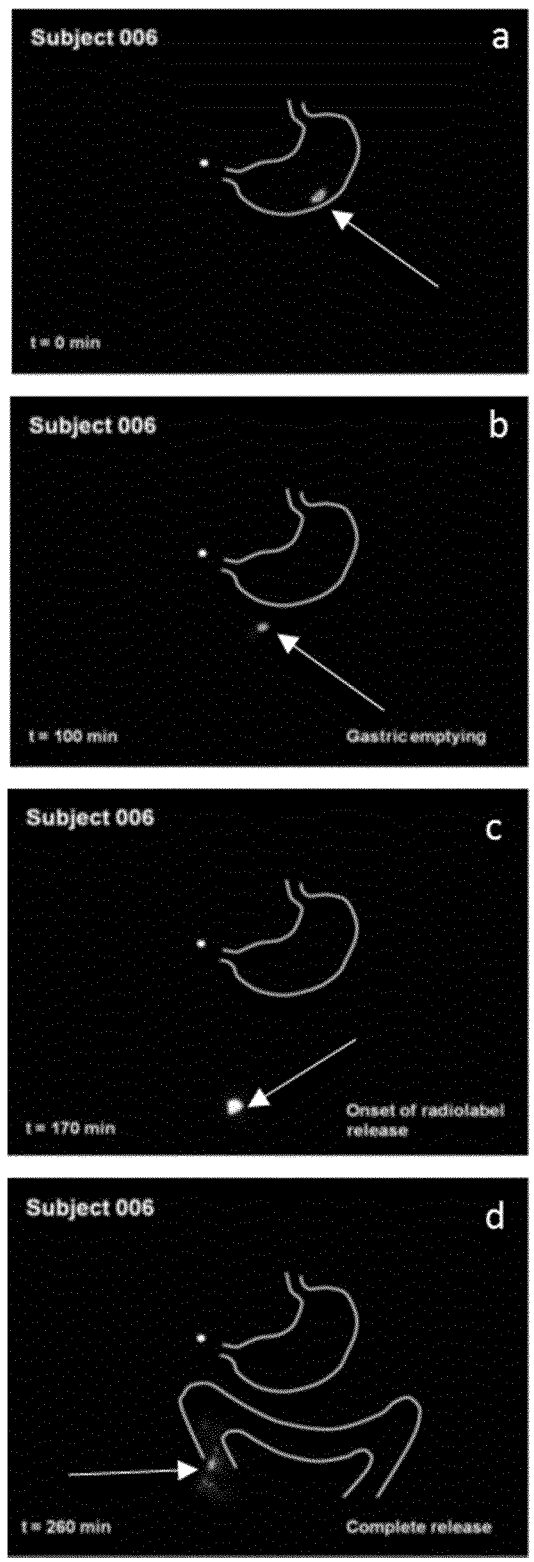
FIG. 3: Scintigraphic imaging of presently disclosed pharmaceutical composition (OC5) capsule release in the gastrointestinal tract of a human volunteer.

FIG. 3 shows images representative of the results obtained in the study, i.e. illustrating key events occurring in the gastrointestinal transit of the capsule.

The key events illustrated in FIG. 3(a)-(d) are anterior scintigraphic images of the gastrointestinal transit of the OC5 capsule in Subject 006 at various times post oral intake: (a) At t=0 min, after oral intake, the capsule is intact and located in the stomach, as shown by the distinct trace of the capsule. (b) At t=100 min, confirmation of capsule gastric emptying; i.e. the capsule has left the stomach. The trace of the capsule is still distinct. (c) At t=170 min, onset of disintegration and capsule content release in the small intestine, as visualised by a larger trace around the capsule. (d) At t=260 min, complete disintegration and capsule content release in the ascending colon, as evidenced by the larger spread of the trace. The white arrow drawn in each of the images (a)-(d) points at the radioactive trace of the capsule. Stomach and colon outlines are drawn for visualisation purposes only. The white filled circle located to the left of the stomach is used as a position marker.

Clinical Double Blind Study Using the Novel Formulation
Study Design

The OC5 study was a randomised, placebo-controlled, double-blind study (OC5-DB-01), run in Germany, the UK and France.

A dose of OC5 consisted of one capsule containing not less than $10^9$ colony-forming units (CFU) of *O. formigenes* with a capacity to metabolise not less than 100 mmol per dose (capsule), read at 19 hours. The placebo product had the same appearance and release properties as the active product and consisted of enteric-coated, size 4 capsules filled with microcrystalline cellulose. During the treatment period, patients provided 24-h urine samples at treatment weeks 2, 4, 6, 8 and 10 (if needed). Stool samples and plasma samples were collected at treatment weeks 4 and 8. To ensure that there was an eligible urine collection at the end of the treatment period, treatment was extended to 10 weeks to obtain an additional collection, if the urine collection at treatment week 8 was considered ineligible.

Inclusion Criteria

Eligible male or female patients were ≥2 years of age (≥5 years in the UK) with a diagnosis of PH type 1, 2 or 3 (as determined by standard diagnostic methods) and a mean urinary oxalate (Uox) excretion ≥1.0 mmol/24 h/1.73 $m^2$, based on at least three eligible urine collections performed during baseline (baseline weeks 1-4 before start of treatment). Patients needed to have an estimated glomerular filtration rate (eGFR)≥40 mL/min/1.73 $m^2$ or a creatinine clearance ≥40 mL/min/1.73 $m^2$ at baseline for inclusion into the study.

Patients taking vitamin B6 (pyridoxine) had to have been taking a stable dose for at least 3 months before screening and were not to change the dose during the study. Patients not receiving vitamin B6 at study entry were required to refrain from initiating pyridoxine for the duration of the study.

Statistical Methods

Statistical analyses of the primary endpoint (change in urinary oxalate excretion from baseline to week 8 of treatment) were performed with a mixed-model repeated measures (MMRM) analysis of covariance that included the following fixed effects: treatment group, baseline urinary oxalate value, visit and visit by-treatment interaction. This change was compared between OC5 and placebo after 8 weeks of treatment. All secondary endpoints based on changes from baseline to end of treatment (change in urinary oxalate levels in subsets of subjects, change in plasma oxalate levels, change of number of *O. formigenes* in faeces) were analysed using the same methodology as for the primary endpoint. Change in number of *O. formigenes* in faeces from baseline to Week 8 of treatment was evaluated using descriptive statistics.

All efficacy analyses were performed on randomised patients who received at least one dose of study medication and who provided at least one eligible measurement of urinary oxalate during treatment with OC5/placebo.

Results

Study Population

Forty-four patients were screened. The main reason for screen failure was a urinary oxalate excretion below 1 mmol/24 h/1.73 m$^2$ during baseline. Twenty-eight patients were randomised; 14 patients received OC5 and 14 patients received placebo and all patients completed the study.

There was a clear relationship between patient age and kidney function, consistent with disease progression. Across both groups, the majority of the patients under 18 years of age (15 out of 19) had a normal kidney function (eGFR≥90 mL/min/1.73 m$^2$) whereas only three out of nine patients aged ≥18 years had a normal kidney function.

Differences in group compositions showed that the OC5 group had a lower mean eGFR (97.47 mL/min/1.73 m$^2$) than the placebo group (123.11 mL/min/1.73 m$^2$).

History of renal and urinary disorders was higher in the OC5 group (11 patients, 79%) than the placebo group (eight patients, 57%), which could be explained by the differences in renal function between groups at baseline.

TABLE 3

Summary of general and renal medical history

|  | OC5 (N = 14) n (%) | Placebo (N = 14) n (%) | Total (N = 28) n (%) |
| --- | --- | --- | --- |
| Any other medical history | 12 (85.7) | 11 (78.6) | 23 (82.1) |
| Renal and urinary disorders | 11 (78.6) | 8 (57.1) | 19 (67.9) |

TABLE 3-continued

Summary of general and renal medical history

|  | OC5 (N = 14) n (%) | Placebo (N = 14) n (%) | Total (N = 28) n (%) |
| --- | --- | --- | --- |
| Calculus urinary | 6 (42.9) | 2 (14.3) | 8 (28.6) |
| Dysuria | 0 | 1 (7.1) | 1 (3.6) |
| Haematuria | 2 (14.3) | 0 | 2 (7.1) |
| Hydronephrosis | 1 (7.1) | 0 | 1 (3.6) |
| Hypercalciuria | 0 | 1 (7.1) | 1 (3.6) |
| Hyperoxaluria | 1 (7.1) | 1 (7.1) | 2 (7.1) |
| Nephrocalcinosis | 5 (35.7) | 5 (35.7) | 10 (35.7) |
| Nephrolithiasis | 7 (50.0) | 4 (28.6) | 11 (39.3) |
| Proteinuria | 2 (14.3) | 1 (7.1) | 3 (10.7) |
| Renal colic | 2 (14.3) | 0 | 2 (7.1) |
| Renal failure | 0 | 1 (7.1) | 1 (3.6) |
| Renal failure chronic | 4 (28.6) | 0 | 4 (14.3) |
| Renal impairment | 2 (14.3) | 1 (7.1) | 3 (10.7) |
| Renal pain | 1 (7.1) | 0 | 1 (3.6) |

Medical history is coded according to MedDRA version 16.1

Change in Urinary Oxalate Excretion

When studying the placebo group versus the treated group in the results below, it can be seen that an improved effect was provided by the OC5 pharmaceutical composition as compared to the previous OC3 formulation.

It was anticipated that the OC5-treated group would decrease more in urinary oxalate per urinary creatinine than the placebo group. However, instead, the OC5 group increased in urinary oxalate excretion per urinary creatinine excretion while the placebo group decreased. At treatment week 8, the difference between the OC5 and Placebo groups achieved statistical significance (p=0.030). The surprising increase in the OC5 group indicates an enhanced excretion of oxalate and a mobilization of oxalate deposits (Table 4) that did not occur in studies with the previous OC3 formulation. Mobilization of deposits also forms part of a series of events where a decrease in free oxalate concentration in plasma shifts the equilibrium of oxalate in the PH patients towards mobilisation of deposits. This is particularly evident in PH patients with low kidney function (low eGFR).

TABLE 4

Analysis of change from baseline in the ratio of urinary oxalate excretion to urinary creatinine excretion by week and treatment

OC5-DB-01

Change from baseline in the ratio (mg/g) of urinary oxalate excretion to urinary creatinine excretion

| Treatment Week | Parameter[1] | OC5 (N = 14) | Placebo (N = 14) | OC5 − placebo |
| --- | --- | --- | --- | --- |
| Week 2 (Study Week 8) | LS Mean (SE) p-value | −6.61 (6.721) 0.859 | −8.35 (6.981) — | +1.74 |
| Week 4 (Study Week 10) | LS Mean (SE) p-value | −5.39 (6.443) 0.686 | −9.07 (6.273) — | +3.68 |
| Week 6 (Study Week 12) | LS Mean (SE) p-value | −1.96 (5.625) 0.451 | −8.14 (5.780) — | +6.18 |
| Week 8 (Study Week 14) | LS Mean (SE) p-value | 5.41 (6.092) 0.030 | −15.96 (7.010) — | +21.37 |

TABLE 4-continued

Analysis of change from baseline in the ratio of urinary oxalate
excretion to urinary creatinine excretion by week and treatment

OC3-DB-02

Change from baseline in the ratio (mmol/mol) of urinary
oxalate excretion to urinary creatinine excretion

| | Parameter[2] | OC3 (N = 21) | Placebo (N = 13) | OC3 − placebo |
|---|---|---|---|---|
| Week 8 | Mean (SD) | 4.74 (38.20) | −1.67 (31.79) | +6.41 |
| | p-value | 0.607 | — | |

[1]Repeated measures analysis;
[2]Wilcoxon-Mann-Whitney analysis
LS: Least square;
SE: Standard error;
SD: Standard deviation The table shows that the difference between OC5 and placebo in the ratio of urinary oxalate excretion to urinary creatinine excretion increased over time from baseline and was statistically significant for OC5 at treatment week 8 in the OC5-DB-01 study (p=0.030, using repeated measures analysis). For OC3, the difference between OC3 and placebo in the change in ratio of urinary oxalate excretion to urinary creatinine excretion ratio from baseline at treatment week 8 in the OC3-DB-02 study was not statistically significant (p=0.607, using Wilcoxon-Mann-Whitney analysis).

Change in *Oxalobacter* Count

*Oxalobacter formigenes* is a naturally occurring type of bacteria. There are two known genotypes of *Oxalobacter*, type 1 and type 2. The strain HC-1 in OC5 is of the *Oxalobacter formigenes* genotype 1. The numbers of *Oxalobacter formigenes* of both genotypes were measured using a quantitative real-time polymerase chain reaction method. Only one patient (who was in the OC5 treated group) had detectable *O. formigenes* genotype 1 at the start of the study. At treatment week 8, 13 out of 14 patients in the OC5 group showed substantial levels of *O. formigenes* genotype 1 count. The patient with no increase in *O. formigenes* type 1 at treatment week 8, however had increased levels at treatment week 4. Genotype 1 bacteria were not detected in any patients in the placebo group at any time during the study.

Three patients in the OC5 group and three patients in the placebo group had detectable levels of *O. formigenes* genotype 2 during baseline. *O. formigenes* genotype 2 started to grow in the OC5 group but not in the placebo group indicating that OC5 mediates a transfer of excess oxalate from plasma to the intestine, thereby also feeding *O. formigenes* of the genotype 2.

The least square (LS) mean difference between the change in number of *O. formigenes* in faeces from baseline to Week 8 was $1.27 \times 10^7$ cells/g greater in the OC5 group than in the placebo group (95% CI: $4.79 \times 10^6$-$2.07 \times 10^7$; p<0.0002) (Table 5).

TABLE 5

Change in total number of *O. formigenes* in faeces after 8 weeks of treatment (cells/g)

| | Change in number of *O. formigenes* | | Difference to Placebo | | |
|---|---|---|---|---|---|
| Treatment | LS mean | 95% CI | LS mean | 95% CI | p-value |
| OC5 | 13,814,394 | 7,992,437-19,636,352 | 12,723,497 | 4,788,219-20,658,775 | 0.00023 |
| Placebo | 1,090,897 | −4,293,285-6,475,081 | — | — | — |

CI: Confidence interval,
LS: Least square
Based on a mixed-model repeated measures analysis of variance including treatment, visit and visit by treatment interaction and baseline number of *O. formigenes* as a covariate.
Baseline level of *O. formigenes* was defined as last non missing and valid assessment before first dose of study drug.

Change in Plasma Oxalate Concentration and Correlation with Kidney Function

The correlation between plasma oxalate and kidney function at baseline was highly statistically significant (Table 6).

TABLE 6

Correlation between plasma oxalate concentration and kidney function (eGFR) at baseline
Correlation between plasma oxalate and eGFR

| Study | # patients | p-value |
|---|---|---|
| OC5-DB-01 | 28 | 0.007 |

For the full study population, there was a negative correlation between baseline plasma oxalate and eGFR (r=−0.508, p<0.007). Mean plasma oxalate concentration for the full study population was 14.7 μmol/L. Patients with eGFR>90 mL/min/1.73 m² had a mean plasma oxalate concentration of 10.2 μmol/L whereas those patients with an eGFR<90 mL/min/1.73 m² had a mean plasma oxalate concentration of 23.7 μmol/L. In the OC5-DB-01 study, the placebo group with advancing disease (eGFR<95 mL/min/1.73 m²) increased in plasma oxalate concentration with +2.95 μmol/L over 8 weeks, while the OC5 group already after 8 weeks did not increase to the same extent. Plasma oxalate concentration is negatively correlated with kidney function (Table 6 above). Since decrease in kidney function is indicative of PH progression, change in plasma oxalate is also a measure of advancement of the disease. Plasma oxalate accumulation followed by calcium oxalate crystallisation is ultimately the driver of the disease. By impacting on the increase in plasma oxalate concentration over time, OC5 may delay or stop the disease progression (Table 7).

TABLE 7

Summary of repeated measures analysis of change from baseline in plasma oxalate concentration (μmol/L) in the OC5-DB-01 study and subgroups with low kidney function

| Study | Duration weeks | Placebo Change in plasma oxalate, μmol/L | OC5 Change in plasma oxalate, μmol/L | Placebo − OC5 |
|---|---|---|---|---|
| OC5-DB-01 | 8 | <+1 | <+1 | |
| patients eGFR < 95 mL/min/1.73 m² | 8 | +2.95 | +0.66 | +2.29 |
| patients eGFR < 65 mL/min/1.73 m² | 4 | <+1 | <+1 | +7.18 |
|  | 8 | +8.7 | +1.52 | |

Change in Plasma Oxalate Concentration and Correlation with *Oxalobacter* Count

There was a negative correlation between change in plasma oxalate concentration and change in *O. formigenes* genotype 1 such that the plasma oxalate concentration decreased with increased *Oxalobacter* genotype 1 count. This correlation achieved statistical significance (max. r=0.624; p=0.040) (Table 8) at treatment week 4. This finding suggests that the introduced *O. formigenes* bacteria are able to metabolise free oxalate that originates from plasma.

TABLE 8

Correlation between the change in plasma oxalate concentration from baseline (μmol/L) and change in *O. formigenes* genotype 1 from baseline

| Treatment Week | OC5 (N = 14) N | R | P |
|---|---|---|---|
| Week 4 | 11 | −0.624 | 0.040 |
| Week 8 | 10 | −0.148 | 0.684 |

Change is calculated as post-baseline value minus baseline value.
Correlations are Pearson's r values.

Impact on Kidney Function

In patients with baseline eGFR<90 mL/min/1.73 m², there was a tendency for blood urea nitrogen (BUN) concentration to decrease from baseline in the OC5 group and increase in the placebo group (LS mean difference from baseline after 8 weeks, OC5: −3.95 mg/dL; placebo: 5.24 mg/dL; p=0.085) (Table 9).

TABLE 9

Repeated measures analysis of change from baseline in blood urea nitrogen (mg/dL) in patients with baseline eGFR <90 mL/min/1.73 m²

| Treatment | | Change from baseline in Blood Urea Nitrogen (mg/dL) | |
|---|---|---|---|
| Week | Parameter | OC5 | Placebo |
| Week 4 | N | 6 | 3 |
|  | LS Mean (SE) | −3.19 (2.202) | 4.29 (3.278) |
|  | p-value | 0.095 | — |

TABLE 9-continued

Repeated measures analysis of change from baseline in blood urea nitrogen (mg/dL) in patients with baseline eGFR <90 mL/min/1.73 m²

| Treatment | | Change from baseline in Blood Urea Nitrogen (mg/dL) | |
|---|---|---|---|
| Week | Parameter | OC5 | Placebo |
| Week 8 | N | 7 | 3 |
|  | LS Mean (SE) | −3.95 (2.566) | 5.24 (3.920) |
|  | p-value | 0.085 | — |

LS: Least square;
eGFR: Estimated glomerular filtration rate;
SE: Standard error Least squares mean difference from baseline in urine output volume between the OC5 and placebo groups at treatment week 2 was −235.2 mL in the OC5 group and +242.3 mL in the placebo group; this difference achieved statistical significance (p=0.039). At treatment week 6, LS mean difference from baseline in urine output between the OC5 and placebo groups was −453.7 mL in the OC5 group and +375.4 mL in the placebo group and this too achieved statistical significance (p=0.001) (Table 10). At week 8, the difference was a strong trend, but did not reach statistical significance (p=0.141). All patients, both patients treated with active (OC5) and patients treated with placebo in the study had the same instructions regarding fluid intake.

TABLE 10

Repeated measures analysis of change from baseline in urine volume (mL)

| Treatment | | Change from baseline in urine volume (mL) | |
|---|---|---|---|
| Week | Parameter | OC5 (N = 14) | Placebo (N = 14) |
| Week 2 | LS Mean (SE) | −235.2 (149.93) | 242.3 (160.16) |
|  | p-value | 0.039 | — |
| Week 4 | LS Mean (SE) | −246.0 (176.66) | −163.0 (172.71) |
|  | p-value | 0.739 | — |
| Week 6 | LS Mean (SE) | −453.7 (160.23) | 375.4 (165.13) |
|  | p-value | 0.001 | — |
| Week 8 | LS Mean (SE) | −392.2 (139.72) | −82.7 (148.25) |
|  | p-value | 0.141 | — |

LS: Least square;
SE: Standard error
Urine volume is the volume of urine collected in one 24-h period.

These post hoc analyses indicated that OC5 treatment had possible clinical benefit. The reduced BUN and decreased urine output in the OC5 group suggest that renal water reabsorption and urine-concentrating ability were improving in these patients. The recent publication from Zhao et al., 2016, concludes that urinary volume is generally increased in PH-patients and that urinary volume at the time of diagnosis correlates negatively with the eGFR (p=0.001). While higher volume might reflect recommendations to increase fluid intake for PH patients, the authors suggest an alternative interpretation that the increased urinary volumes reflect decreased urinary-concentrating abilities among PH-patients who have established tubulointerstitial injury. Our findings support these observations, and OC5 treatment would indicate a beneficial treatment effect for the water reabsorption ability of kidneys. Blood urea nitrogen (BUN), being a marker for tubular injury, is highly elevated in PH-patients. The finding that OC5 treatment tended to reduce BUN could also indicate a beneficial treatment effect for the kidney.

Impact on Inflammatory Markers

Calcium oxalate crystals are known to cause inflammatory responses [Worcester et al., 2013; Anders et al., 2013]. There was a tendency for the number of total leukocytes to decrease in OC5-treated patients and increase in placebo-treated patients from baseline (p=0.067 at week 8). The difference in change in eosinophils from baseline was statistically significant at treatment week 8 (p=0.044). There was a tendency also for the number of lymphocytes to decrease in OC5-treated patients and increase in placebo-treated patients (Table 11). The significant decrease of eosinophils and the tendency for leukocyte and lymphocyte counts to decrease in the OC5-treated patients and increase in placebo-treated patients over 8 weeks indicated that *O. formigenes* treatment has effects on PH-associated inflammation. However, when comparing the effects of the two formulations OC3 and OC5 it is clear that OC5 has an improved effect already after 8 weeks of treatment. Furthermore, as indicated in Table 11, there was no positive trend for OC3.

TABLE 11

Summary of repeated measures analysis of change from baseline in number of white blood cells (OC5-DB-01)

| Treatment Week | Parameter | OC5 (N = 14) | Placebo (N = 14) | OC5 − placebo | OC3 − placebo OC3-DB-02 (see Table 15) |
|---|---|---|---|---|---|
| Total leukocytes ($10^9$/L) | | | | | |
| Week 4 | LS Mean (SE) | −0.23 (0.389) | 0.49 (0.375) | −0.72 | |
| | P-value | 0.196 | — | | |
| Week 8 | LS Mean (SE) | −0.28 (0.565) | 1.26 (0.565) | −1.54 | −0.45 |
| | P-value | 0.067 | — | | 0.338 |
| Lymphocytes ($10^9$/L) | | | | | |
| Week 4 | LS Mean (SE) | −0.15(0.132) | 0.19 (0.128) | −0.34 | |
| | P-value | 0.071 | — | | |
| Week 8- | LS Mean (SE) | −0.20 (0.187) | 0.27 (0.187) | −0.47 | |
| | P-value | 0.089 | — | | |
| Eosinophils ($10^9$/L) | | | | | |
| Week 4 | LS Mean (SE) | −0.06 (0.036) | 0.00 (0.036) | −0.06 | |
| | P-value | 0.267 | — | | |
| Week 8 | LS Mean (SE) | −0.06 (0.042) | 0.07 (0.042) | −0.13 | |
| | P-value | 0.044 | — | | |

LS: Least square;
SE: Standard error

Open Label Clinical Study Using the Novel Formulation

The clinical development plan for OC5 also includes a phase 2, open-label, multi-centre study to evaluate the efficacy of OC5 to reduce plasma oxalate in subjects with primary hyperoxaluria who are on dialysis. Patients are treated for 6 weeks with study drug, with 4 weeks of baseline measurements prior to initiation of study medication and 4 weeks of measurement after drug administration. Thereafter, extension of the treatment is continued on a yearly basis.

One of the patients is a 59-year old male with very high baseline plasma oxalate. During the first one year extension of the study, the ratio between total and soluble plasma oxalate decreased from 2.5 to 1.9. The amount of free plasma oxalate has plateaued several times around the calcium oxalate saturation limit, 50-60 μmol/L, each time followed by an increase in total plasma oxalate concentration in the next measurement (i e from week 4 to week 5, weeks 16-20 to week 24, week 32 to week 36 and week 40 to week 44 (Table 12). These findings suggest that as various compartments of oxalate tissue deposits are dissolving, oxalate is first saturating plasma proteins and then is transferred to free plasma oxalate. As *Oxalobacter* is withdrawing free plasma oxalate into the intestines, more oxalate is set free from plasma proteins.

TABLE 12

Total and soluble (free) plasma oxalate (Pox; μmol/L) over time during treatment with *Oxalobacter formigenes*

| Week | Total Pox (μmol/L) | Free Pox (μmol/L) | Ratio |
|---|---|---|---|
| 0 | 162 | 64 | 2.5 |
| 4 | 134 | 55 | 2.4 |
| 8 | 155 | 78 | 2.0 |
| 12 | 125 | 68 | 1.8 |
| 16 | 124 | 45 | 2.8 |
| 20 | 112 | 50 | 2.2 |
| 24 | 137 | 59 | 2.3 |
| 28 | 138 | 60 | 2.3 |

TABLE 12-continued

Total and soluble (free) plasma oxalate (Pox; μmol/L) over time during treatment with *Oxalobacter formigenes*

| Week | Total Pox (μmol/L) | Free Pox (μmol/L) | Ratio |
|---|---|---|---|
| 32 | 126 | 57 | 2.2 |
| 36 | 137 | 67 | 2.0 |
| 40 | 121 | 60 | 2.0 |
| 44 | 154 | 79 | 1.9 |
| 48 | 164 | 86 | 1.9 |
| 52 | 144 | 74.3 | 1.9 |

Analysis of Previous Clinical Studies and Integrated Analysis of Studies Using Previous and Present Pharmaceutical Formulations Change in Plasma Oxalate Concentration Using the Previous OC3 Formulation In a previous study with OC3, it was shown that the natural progression in plasma oxalate for the placebo group over 24 weeks was +3.25 μmol/L for patients who had a baseline eGFR<90 mL/min/1.73 m$^2$.

The OC3 treated group was stable or reducing in plasma oxalate concentration indicating a slower or stopped disease progression. (Table 13).

TABLE 13

Summary of repeated measures analysis of change from baseline in plasma oxalate concentration (μmol/L) using the previous OC3 formulation (study OC3-DB-02 and subgroups with low kidney function)

| Study | Duration Weeks | Placebo Change in plasma oxalate, μmol/L | OC3 Change in plasma oxalate, μmol/L |
|---|---|---|---|
| OC3-DB-02 | 24 | +0.14 | −1.54 |
| patients eGFR < 90 mL/min/1.73 m$^2$ | 8 | +1.80 | +0.50 |
|  | 24 | +3.25 | −1.71 |
| patients eGFR < 60 mL/min/1.73 m$^2$ | 8 | +13.10 | +1.28 |
|  | 24 | +15.00 | −2.58 |

Change in Calcium Excretion in Integrated Analysis of all Double Blind Studies Done Upon the unexpected findings that the OC5 group increased in urinary oxalate excretion per urinary creatinine excretion while the placebo group decreased and that OC5 may impact on the accumulation rate of plasma oxalate concentration over time, an integrated analysis was made over all double blind studies with *Oxalobacter formigenes* treatment. Data in the integrated analysis of our double blind studies with OC3 and OC5 vs placebo show that urinary calcium excretion increased over time in patients with low kidney function, i e patients that are likely to have accumulated oxalate deposits (eGFR<90 ml/min/1.73 m$^2$). This finding is statistically significant (p=0.007) (Table 14).

TABLE 14

Change in calcium excretion (μmol/24 h) in response to treatment with *Oxalobacter formigenes*

| | Change in Ca$^{2+}$ excretion, μmol/24 h | | | |
|---|---|---|---|---|
| | Active (OC3 or OC5) | Placebo | p-value | N Active (OC3 or OC5)/ placebo |
| Patients with eGFR < 90 mL/min/1.73 m$^2$ | +30 | −70 | 0.007 | 19/11 |

Without wishing to be bound by theory, it is postulated that *Oxalobacter* treatment, through the mechanism of removing free oxalate from plasma, mobilises calcium oxalate deposits. The findings that oxalate excretion and calcium excretion increase in the clinical studies support this hypothesis.

Impact on Inflammatory Markers

Similarly to the findings for OC5 treatment, OC3 treatment impact on inflammatory markers. In the OC3-DB-02 study (Table 15) there was a significant reduction of leucocytes in the OC3 treated arm after 24 weeks treatment. The difference to placebo was still significant 4 weeks after treatment stop. However, when comparing the effects of the two formulations OC3 and OC5 it is clear that OC5 has an improved effect already after 8 weeks of treatment.

TABLE 15

Impact on inflammatory markers in response to OC3 treatment

| OC3-DB-02 study Week | OC3 mean change 10$^9$ cells/L (N = 21) | Placebo mean change 10$^9$ cells/L (N = 13) | OC3 − placebo | p-value | OC5 − placebo (see Table 11) |
|---|---|---|---|---|---|
| Leukocytes week 8 | −0.34 | +0.11 | −0.45 | 0.338 | −1.54 |
| Leukocytes week 24 | −0.85 | +1.05 | −1.90 | 0.013 | |
| Leukocytes week 28 (after 4 weeks off treatment) | −0.66 | +0.75 | −1.41 | 0.045 | |

REFERENCES

Aggarwal K P. Narula S, Kakkar M and Tandon C. Nephrolithiasis: Molecular mechanism of renal stone formation and the critical role played by modulators. BioMed Res Int Vol 2013, Article ID 292953, 21 pages, 2013.

Beck B B, Hoyer-Kuhn H, Gael H, Habbig S, Hoppe B (2014) Hyperoxaluria and systemic oxalosis: an update on current therapy and future directions. Expert opin. Investig Drugs, January 22(1): 117-29.

Belostotsky R, Seboun E, Idelson Milliner D S, Becker-Cohen R, Rinat C, Monico C G, Feinstein S, Ben-Shalom E, Magen D, Weissman I, Charon C, and Frishberg Y (2010) Mutations in DHDPSL Are Responsible For Primary Hyperoxaluria Type III. Am J Hum Gen 87, 392-399.

Bhasin B, Ürelkli H M, Atta M G. Primary and secondary hyperoxaluria: Understanding the enigma. World J Nephrol 2015 May 6; 4(2):235-44. doi: 10.5527/wjn.v4.i2.235.

Cochat P, Deloraine A, Rotily M, Olive F, Liponski I, Deries N (1995) Epidemiology of primaryhyperoxaluria type 1. Nephrol Dial Transplant 10:Suppl 8:3-7.

Cochat P, Hulton S A, Acquaviva C, Danpure C J, Daudon M, De Marchi M, Fargue S, Groothoff J, Harambat J, Hoppe B, Jamieson N V, Kemper M J, Mandrile G, Marangella M, Picca S, Rumsby G, Salido E, Straub M, van Woerden C S (2012) Primary hyperoxaluria Type 1: indications for screening and guidance for diagnosis and treatment. Nephrol Dial Transplant 27:1729-1736.

Cochat P, Rumsby G (2013) Primary Hyperoxaluria. N Engl J Med 369:649-658.

Gregory J G, Starkloff E B, Miyai K, Schoenberg H W. Urological complications of ileal bypass operation for morbid obesity. J Urology 1975; 113: 521-524.

Harambat J, Fargue S, Acquaviva C, Gagnadoux M F, Janssen F, Liutkus A, Mourani C, Macher M A, Abramowicz D, Legendre C, Durrbach A, Tsimaratos M, Nivet H, Girardin E, Schott A M, Rolland M O, Cochat P (2010) Genotype-phenotype correlation in primary hyperoxaluria type 1: the p.Gly170Arg AGXT mutation is associated with a better outcome. Kidney Int 77:443-449.

Hatch M and Freel R W. The Roles and Mechanisms of Intestinal Oxalate Transport in Oxalate Homeostasis. Semin Nephrol. 2008 March; 28(2): 143-151.

Hatch M, Gjymishka A, Salido E C, Allison M J, Freel R W. Enteric oxalate elimination is induced and oxalate is normalized in a mouse model of P H following intestinal colonization with *Oxalobacter*. AJPGLP, 2011; 300 G461-G469.

Hatch M and Freel R, A human strain of *Oxalobacter* (HC-1) promotes enteric oxalate secretion in the small intestine of mice and reduces urinary oxalate excretion. Urolithiasis, 2013; August 20 (E publication).

Hopp K, Cogal A G, Bergstralh E J, Seide B M, Olson J B, Meek A M, Lieske J C, Milliner D S, Harris P C Rare Kidney Stone Consortium (2015) Phenotype-Genotype Correlations and Estimated Carrier Frequencies of Primary Hyperoxaluria. J Am Soc Nephrol 26:2559-2570.

Hoppe B, Beck B, Gatter N, von Unruh G, Tischer A, Hesse A, Laube N, Kaul P, Sidhu H (2006) *Oxalobacter formigenes*: a potential tool for the treatment of primary hyperoxaluria type 1. Kidney Int 70:1305-1311.

Hoppe B, Beck B and Milliner D (2009) The Primary Hyperoxalurias. Kidney Int 75:1264-1271.

Hoppe B, Groothoff J W, Hulton S A, Cochat P, Niaudet P, Kemper M J, Deschênes G, Unwin R, Milliner D (2011) Efficacy and safety of *Oxalobacter formigenes* to reduce urinary oxalate in primary hyperoxaluria. Nephrol Dial Transplant 26:3609-3615.

Kopp N, Leumann E (1995) Changing pattern of primary hyperoxaluria in Switzerland. Nephrol Dial Transplant 10:2224-2227.

Lagies R, Beck B, Hoppe B, Sreeram N, Udink ten Care F, Apical sparing of longitudinal strain, left ventricular rotational abnormalities and short-axis dysfunction in primary hyperoxaluria type 1. Circ. Heart Failure, 6, e45-e47, 2013.

Lagies R, Udink ten Cate F, Hoppe B, Feldkotter M, Beck B, Herberg U, Speckle tracking echocardiography detects impaired systolic function in patients with primary hyperoxaluria Type 1, (Poster from P H Workshop, Chicago, 2014).

Lagies R, Beck B, Hoppe B, Sheta S, Weiss V, Sreeram N and Udink ten Cate F. Inhomogenous longitudinal cardiac rotation and impaired left ventricular longitudinal strain in children and young adults with end stage renal failure undergoing hemodialysis. Echocardiography, 32(8), 1250-1260, 2015.

Leumann E and Hoppe B (2001) The Primary hyperoxalurias, J Am Soc Nephrol 12:1986-1993.

Lieske J C, Monico C G, Holmes W S, Bergstralh E J, Slezak J M, Rohlinger A L, Olson J B, Milliner D S (2005) International registry for Primary Hyperoxaluria, Am J Nephrol 25:290-296.

Pascual E, Sivera F. Time required for disappearance of urate crystals from synovial fluid after successful hypouricaemic treatment relates to the duration of gout. Ann Rheum Dis. 2007 August; 66(8):1056-8. Epub 2007 Jan. 12.

Stewart C S, Duncan S H, Cave D R. *Oxalobacter formigenes* and its role in oxalate metabolism in the human gut. FEMS Microbiology Letters 230 (2004) 1-7

Tang X, Bergstralh E J, Mehta R A, Vrtiska T J, Milliner D S, Lieske J C (2015) Nephrocalcinosis is a risk factor for kidney failure in primary hyperoxaluria. Kidney Int 87:623-631.

van Woerden C S, Groothoff J W, Wanders R J, Davin J C, Wijburg F A (2003) Primary hyperoxaluria type 1 in the Netherlands: prevalence and outcome. Nephrol Dial Transplant 18:273-279.

van Woerden C S, Groothoff J W, Wiiburg F A, Duran M, Wanders R J, Barth P G, Poll—The B T. High incidence of hyperoxaluria in generalized peroxisomal disorders. Mol Geet Metab 2006 August; 88(4):346-50. Epub 2006 Apr. 18.

Worcester E, Evan A, Coe F, Lingeman J, Krambeck A, Sommers A, Phillips C and Milliner D (2013) A test of the hypothesis that oxalate secretion produces proximal tubule crystallization in primary hyperoxaluria type 1. Am J Physiol Renal Physiol 305, FI574-584.

Zhao F, Bergstralh E J, Mehta R A, Vaughan L E, Olson J B, Seide B M, Meek A M, Cogal A G, Lieske J C, Milliner D S, Investigators of the Rare Kidney Stone Consortium (2016) Predictors of incident ESRD among patients with primary hyperoxaluria presenting prior to kidney failure. Clin J Am Soc Nephrol 11:119-126.

The invention claimed is:

1. An enteric-coated capsule for oral administration of *Oxalobacter formigenes* to a subject in need thereof, comprising a pharmaceutical composition comprising:
   (i) 10% to 25% by dry weight of *Oxalobacter formigenes*;
   (ii) 50% to 65% by dry weight of sucrose;
   (iii) about 10% to 30% by dry weight of one or more cryopreserving agents and/or excipients;
   wherein said enteric-coated capsule delivers *Oxalobacter formigenes* to the small intestine and/or to the ileum, and
   wherein the in vitro oxalate-degrading activity of the *Oxalobacter formigenes* present in said enteric-coated capsule is no less than (NLT) 100 mmol/capsule/19 hours.

2. The enteric-coated capsule according to claim 1, wherein said pharmaceutical composition comprises 15% to 25% by dry weight of *Oxalobacter formigenes*.

3. The enteric-coated capsule according to claim 2, wherein said pharmaceutical composition comprises 17% to 22% by dry weight of *Oxalobacter formigenes*.

4. The enteric-coated capsule according to claim 1, wherein the cryopreserving agents and/or excipients are selected from maltodextrin, oligofructose, and alginate.

5. The enteric-coated capsule according to claim 4, wherein said pharmaceutical composition comprises 15% to 21% by dry weight of maltodextrin as a cryopreserving agent.

6. The enteric-coated capsule according to claim 4, wherein said pharmaceutical composition comprises 16% to 19% by dry weight of maltodextrin as a cryopreserving agent.

7. The enteric-coated capsule according to claim 4, wherein said pharmaceutical composition comprises 1% to 5% by dry weight of oligofructose and 0.5% to 2% by dry weight of alginate as cryopreserving agents.

8. The enteric-coated capsule according to claim 7, wherein said pharmaceutical composition further comprises 1% to 5% by weight of water.

9. The enteric-coated capsule according to claim 4, wherein said pharmaceutical composition comprises 0.5% to 1.5% by dry weight of alginate as a cryopreserving agent.

10. The enteric-coated capsule according to claim 1, wherein said pharmaceutical composition comprises
   (i) 17% to 22% by dry weight of *Oxalobacter formigenes*;
   (ii) 52% to 62% by dry weight of sucrose; and
   (iii) 17% to 25% by dry weight of one or more cryopreserving agents and/or excipients.

11. The enteric-coated capsule according to claim 1, wherein said pharmaceutical composition comprises:
   (i) about 19% by dry weight of *Oxalobacter formigenes;*
   (ii) about 57% by dry weight of sucrose;
   (iii) about 21% by dry weight of one or more cryopreserving agents and/or excipients, and
   (iv) q.s. water.

12. The enteric-coated capsule according to claim 11, wherein said about 21% by dry weight of one or more cryopreserving agents and/or excipients comprises about 1% by dry weight of alginate, about 17% by dry weight of maltodextrin, and about 3% by dry weight of oligofructose.

13. The enteric-coated capsule according to claim 1, wherein said pharmaceutical composition comprises:
   (i) 19%±1-3% by dry weight of *Oxalobacter formigenes;*
   (ii) 57%±1-3% by dry weight of sucrose; and
   (iii) 21%±1-3% by dry weight of one or more cryopreserving agents and/or excipient comprising 1%±1% by dry weight of alginate, 17%±1-3% by dry weight of maltodextrin and by dry weight 3%±1-3% of oligofructose.

14. The enteric-coated capsule according to claim 1, wherein said enteric-coated capsule shows essentially no disintegration within one hour of incubation in Simulated Gastric Fluid (SGF) having a pH of about 1.2±0.1 and comprising about 3.2 mg/ml of pepsin at a temperature of about 37° C., and a start of disintegration of said capsule is detected within about one hour in Simulated Intestinal Fluid (SIF) having a pH of about 6.8±0.1 and comprising about 10 mg/ml of pancreatin at about 37° C.

15. The enteric-coated capsule according to claim 1, wherein said pharmaceutical composition comprises *Oxalobacter formigenes* in an amount of from about $10^9$ to about $10^{10}$ CFU.

16. A method for treating or preventing an oxalate-related disorder, comprising administering a pharmaceutically effective amount of an enteric-coated capsule according to claim 1 to a subject in need thereof.

17. The method of claim 16, wherein said oxalate-related disorder is selected from a calcium-oxalate deposition related disorder involving hyperoxalemia, hyperoxaluria with hyperoxalemia, primary hyperoxaluria, secondary hyperoxaluria, hyperoxalemia, accumulation of oxalate in blood plasma, oxalosis associated with Chronic Kidney Disease (CKD) or end stage renal disease (ESRD), bariatric surgery with jejunal/ileal resection or Roux-en-Y procedures, Zellweger's disease, cancers with jejunal/ileal resection, renal infections with *Aspergillus niger*, ESRD-patients on dialysis, oxalate-related inflammation, cardiac conductance disorders, vulvodynia, idiopathic calcium oxalate kidney stone disease (urothiliasis), inflammatory bowel disease (IBS), Small Intestine Bacterial Overgrowth (SIBS), gastroenteritis, gastritis, enteritis, enterocolitis, ulcerative colitis, Crohn's disease, or an oxalate-related disorder in a patient treated with a gastrointestinal lipase inhibitor.

18. The method of claim 16, wherein the method is effective to increase systemic oxalate excretion in said subject.

19. The method of claim 16, wherein said pharmaceutically effective amount comprises *Oxalobacter formigenes* in an amount of about $10^9$ to about $10^{10}$ CFUs.

20. The method of claim 19, wherein said method comprises administering said pharmaceutically effective amount at least twice a day for a continuous period of time of months or years, or until the levels of plasma oxalate have been lowered, and are maintained at a level of about 1-3 μmol/L.

* * * * *

UNITED STATES PATENT AND TRADEMARK OFFICE
CERTIFICATE OF CORRECTION

PATENT NO. : 10,765,709 B2
APPLICATION NO. : 16/308439
DATED : September 8, 2020
INVENTOR(S) : Elisabeth Lindner et al.

Page 1 of 1

It is certified that error appears in the above-identified patent and that said Letters Patent is hereby corrected as shown below:

In the Claims

Claim 7, at Column 32, Line 55, please delete "cryopreserving agents." and insert --excipients and cryopreserving agents.--

Claim 9, at Column 32, Line 61, please delete "as a cryopreserving agent."

Signed and Sealed this
Nineteenth Day of January, 2021

Andrei Iancu
*Director of the United States Patent and Trademark Office*